United States Patent
Yang et al.

(10) Patent No.: US 11,198,821 B2
(45) Date of Patent: Dec. 14, 2021

(54) MONITORING OF RESIDUAL METALS IN PARAFFINIC FROTH TREATMENT OPERATIONS AND PROCESS CONTROL

(71) Applicants: Xiaoli Yang, Calgary (CA); Shawn Van Der Merwe, Calgary (CA)

(72) Inventors: Xiaoli Yang, Calgary (CA); Shawn Van Der Merwe, Calgary (CA)

(73) Assignee: Fort Hills Energy L.P., Calgary (CA)

( * ) Notice: Subject to any disclaimer, the term of this patent is extended or adjusted under 35 U.S.C. 154(b) by 0 days.

(21) Appl. No.: 16/811,211

(22) Filed: Mar. 6, 2020

(65) Prior Publication Data
US 2020/0332198 A1  Oct. 22, 2020

(30) Foreign Application Priority Data
Apr. 18, 2019 (CA) .................. CA 3040649

(51) Int. Cl.
*C10G 1/04* (2006.01)
*C10G 21/30* (2006.01)
(Continued)

(52) U.S. Cl.
CPC ............. *C10G 1/045* (2013.01); *C10G 1/047* (2013.01); *C10G 21/30* (2013.01); *G01N 21/359* (2013.01);
(Continued)

(58) Field of Classification Search
CPC ....... C10G 1/045–047; G01N 21/3577; G01N 21/359; G01N 33/241; G01N 33/2858
See application file for complete search history.

(56) References Cited

U.S. PATENT DOCUMENTS

| 7,067,811 | B2 * | 6/2006 | Long | G01N 21/359 |
| | | | | 250/339.12 |
| 7,399,406 | B2 * | 7/2008 | Mikula | C10G 1/047 |
| | | | | 208/390 |

(Continued)

FOREIGN PATENT DOCUMENTS

| CA | 2503610 C | 8/2011 |
| CA | 2834980 A1 | 5/2014 |

(Continued)

OTHER PUBLICATIONS

Wallace, D., Tipman. R., Komishke, B., Wallwork, V., Perkins, E., The Canadian Journal of Chemical Engineering, vol. 82, 667-677, 2004.

(Continued)

*Primary Examiner* — Renee Robinson
(74) *Attorney, Agent, or Firm* — King & Partners, PLC

(57) ABSTRACT

Techniques provided herein relate to regulating at least one operating parameter of a paraffinic froth treatment (PFT) operation and controlling the quality of the produced bitumen in response to a determined concentration of at least one residual metal in a PFT process stream. Determination of the residual metal concentration is based on acquired NIR spectral measurements of the PFT process stream. An alkaline agent dosage in primary extraction operation can be for example regulated in response to a difference between a determined calcium concentration and a calcium concentration specification.

28 Claims, 19 Drawing Sheets

(51) Int. Cl.
   *G01N 21/359* (2014.01)
   *G01N 33/28* (2006.01)
   *G01N 21/3577* (2014.01)
   *C10G 21/14* (2006.01)

(52) U.S. Cl.
   CPC ..... *G01N 21/3577* (2013.01); *G01N 33/2858* (2013.01); *C10G 21/14* (2013.01); *C10G 2300/205* (2013.01); *C10G 2300/80* (2013.01)

(56) References Cited

U.S. PATENT DOCUMENTS

| | | | |
|---|---|---|---|
| 8,449,764 B2 * | 5/2013 | Chakrabarty | C10G 1/045 208/337 |
| 8,949,038 B2 * | 2/2015 | Chakrabarty | G01N 33/42 702/25 |
| 2014/0124412 A1 * | 5/2014 | Long | C10G 1/045 208/391 |
| 2014/0197316 A1 * | 7/2014 | Kadali | G01N 21/3577 250/339.11 |

FOREIGN PATENT DOCUMENTS

| | | | | |
|---|---|---|---|---|
| CA | 2893161 | * | 11/2016 | ............. G01N 21/25 |
| CA | 2946027 A1 | | 4/2018 | |

OTHER PUBLICATIONS

Yang, X., Sedgwick, A., Water Chemistry Study in Bitumen Extraction, 2015 Clay Conference, Edmonton, Alberta.

Yang, X., Exploring the Function and Limitation of Sodium Hydroxide as a Primary Process Aid in the Oil Sands Extraction, Oil Sands 2012, Edmonton, Alberta, Aug. 28-30, 2012.

Chow, R., Zhou, J., and Wallace, D., The Rheology of Oil Sands Slurries, 2006 Oil Sands Conference, Edmonton, Alberta, 2006.

Kasongo, T., Role of Fine Clays and Ionic Species in Bitumen Extraction from Oil Sands Ores Using the Hot Water Extraction Process, Ph. D dissertation, Edmonton, Alberta, U of A, 2006.

Yang, X., Investigation of the Impact of Clays and Heavy Minerals on Ore Processability and Froth Quality, 2013 Clay Workshop Conference, Edmonton, Alberta, Feb. 20-21, 2013.

Kaminsky, H., PhD Thesis, University of Alberta, Fall, 2008.

Sanford E. C., the Canadian Journal of Chemical Engineering, vol. 61, Aug, 554-567, 1983.

Wallace, D., A Physical Chemical Explanation for Deterioration in the Hot Water Processability of Athabasca Oil Sand due to Aging. Fuel Science & Technology International, 699-725 1989.

* cited by examiner

MONITORING OF RESIDUAL METALS IN PARAFFINIC FROTH TREATMENT OPERATIONS AND PROCESS CONTROL

RELATED APPLICATION

The present application claims benefit from the Canadian Patent Application No. 3,040,649 filed on Apr. 18, 2019, that is incorporated herein by reference.

TECHNICAL FIELD

The technical field generally relates to process monitoring and control techniques that may be based on NIR monitored physicochemical parameters of paraffinic froth treatment (PFT) streams in the context of bitumen or heavy oil production.

BACKGROUND

Bitumen froth can be generated from primary separation operations by separating oil sands slurry into a bitumen froth component and a solids-enriched tailings component. This separation can be performed in a flotation unit, for example.

High clay contents in oil sands ore can be responsible for lower bitumen recovery rates, as clay is an undesirable component of bitumen streams and interferes with bitumen separation mechanisms. Processing oil sands ore having a high clay content can lead to reduced bitumen recovery, lower efficiency in terms of primary separation vessel (PSV) performance, and poorer product quality. The addition of an alkaline agent, such as caustic, to increase the pH of the oil sands slurry can enhance bitumen recovery and bitumen froth quality obtained from the primary separation processes.

In subsequent PFT operations, bitumen froth is diluted with a paraffinic solvent and then separated into diluted bitumen and a solvent diluted tailings component in a froth separation unit (FSU), which can include two or three settlers arranged in a counter-current configuration. The diluted bitumen can then be supplied to a solvent recovery unit (SRU) to produce recovered solvent and solvent recovered bitumen, while the solvent diluted tailings component can be supplied to a tailings solvent recovery unit (TSRU) to produce recovered solvent and solvent recovered tailings, which can also be called froth treatment tailings. The solvent recovered tailings can be further processed or can be supplied to a tailings disposal site for settling.

In the context of PFT operations, there are challenges related to monitoring various streams, components and operational parameters, and related to implementing process control strategies which can reduce the likelihood of off-specification streams and ensure quality of the produced bitumen.

SUMMARY

The techniques described herein relate to methods of monitoring various aspects of paraffinic froth treatment (PFT) operations and undertaking operational actions based on these monitored aspects.

In one aspect, there is provided a method for controlling alkaline agent dosage in a primary separation vessel (PSV) that receives an oil sands slurry and produces bitumen froth that is subsequently supplied to a paraffinic froth treatment (PFT) operation that includes PFT process streams. The method includes:

acquiring near infrared (NIR) spectral measurements from an NIR probe located online in at least one of the PFT process streams;

determining a concentration of a residual metal in the at least one PFT process stream based on the acquired NIR spectral measurements;

comparing the determined concentration of residual metal to a concentration specification; and adjusting the alkaline agent dosage for the PSV in response to a difference between the determined concentration of residual metal and the concentration specification.

In some implementations, adjusting the alkaline agent dosage comprises at least one of:

changing a nature of the alkaline agent;
increasing the alkaline agent dosage;
decreasing the alkaline agent dosage; and
modifying water dilution of the oil sands slurry.

Optionally, the at least one PFT process stream is a diluted bitumen overflow from a froth separation unit, a solvent depleted bitumen stream from a solvent recovery unit, or includes both.

In some implementations, the residual metal comprises at least one of iron, calcium, sodium and magnesium. For example, the concentration specification of calcium can be below 10 ppm and the concentration specification of sodium can be below 100 ppm.

In some implementations, the NIR probe is a transmittance probe. For example, the method can include deploying a transmittance type of NIR probe when the PFT operation is in a mature mode and the concentration of the residual metal is expected to be between 1 ppm and 200 ppm. The method can optionally includes changing a type of the NIR probe in response to a change in the determined concentration of the residual metal.

In some implementations, the alkaline agent is caustic soda. In other implementations, the alkaline agent is caustic soda, sodium silicate, sodium bicarbonate, sodium phosphate or any combination thereof.

In some implementations, the method includes adjusting addition of paraffinic solvent into the bitumen froth in response to a difference between the determined concentration of at least one of nickel and vanadium and the concentration specification of the at least one of nickel and vanadium.

In some implementations, the method includes adjusting asphaltene rejection in a froth separation unit in response to a difference between the determined concentration of at least one of nickel and vanadium and the concentration specification of the at least one of nickel and vanadium. Optionally, the method includes obtaining the determined concentration of the at least one of nickel and vanadium in a diluted bitumen overflow from a froth separation unit and/or in a solvent depleted bitumen stream from a solvent recovery unit that recovers solvent from the diluted bitumen overflow; and, in response to an increase in the determined concentration of nickel or vanadium or both, increasing paraffinic solvent addition to obtain an increased solvent-to-bitumen ratio in the bitumen froth and/or increasing asphaltene rejection in the froth separation unit.

In another aspect, there is provided a method for controlling a primary extraction operation used to separate a bitumen froth from an oil sands slurry, the bitumen froth being further separated in a paraffinic froth treatment operation to produce paraffinic froth treatment process streams. The method includes:

determining a calcium concentration of at least one of the paraffinic froth treatment process streams based on online NIR spectral measurements; and controlling alkaline agent dosage into the oil sands slurry in response to the determined calcium concentration when exceeding a predetermined maximum calcium threshold, to provide the at least one paraffinic froth treatment process stream with a calcium concentration below the maximum threshold.

In another aspect, there is provided a method for monitoring quality of bitumen produced by a paraffinic froth treatment (PFT) operation. The method includes:

acquiring NIR spectral measurements from an NIR probe located online in a diluted bitumen overflow stream and/or a bitumen product stream of the PFT operation; and determining a concentration of at least one of vanadium and nickel based on the acquired NIR spectral measurements, wherein the vanadium and nickel are associated with asphaltenes and resins present in the bitumen within the diluted bitumen overflow stream and/or a bitumen product stream and provide a proxy for the quality of the bitumen.

In another aspect, there is provided a method for controlling a bitumen froth treatment operation that produces a diluted bitumen overflow in a froth separation unit and bitumen in a solvent separation unit that recovers solvent from the diluted bitumen overflow. The method includes:

acquiring NIR spectral measurements from an NIR probe located online in at least one of the diluted bitumen overflow and the bitumen;

determining a concentration of at least one of vanadium and nickel based on the acquired NIR spectral measurements;

comparing the determined concentration to a concentration specification; and controlling a quality of the bitumen in response to a difference between the determined concentration and the concentration specification.

In some implementations, the concentration specification of nickel is between 50 and 60 ppm. The concentration specification of vanadium can be between 130 and 160 ppm.

In some implementations, controlling the quality of the bitumen includes increasing asphaltene rejection in the froth separation unit, if the determined concentration is above the concentration specification. Optionally, controlling the quality of the bitumen includes increasing solvent addition to provide a higher solvent-to-bitumen ratio in the bitumen froth that is supplied into the froth separation unit to increase asphaltene precipitation, if the determined concentration is above the concentration specification.

In some implementations, controlling the quality of the bitumen includes regulating at least one operating parameter of the paraffinic froth treatment operation. For example, the at least one operating parameter of the paraffinic froth treatment operation that is regulated in response to the difference between the determined concentration and the concentration specification includes a temperature of the froth separation unit, a type of the paraffinic solvent added to the bitumen froth, a pretreatment of the bitumen froth prior to the froth separation unit, a bitumen content of the bitumen froth prior to the froth separation unit, a settling parameter of the froth separation unit, or a combination thereof.

In some implementations of the methods described herein, the concentration of vanadium and nickel are at low levels below 1000 ppm, 500 ppm, 200 ppm, 100 ppm, 50 ppm, or 30 ppm.

In another aspect, there is provided a process for producing bitumen, comprising:

separating an oil sands slurry in a Primary Separation Vessel (PSV) to produce a bitumen froth and solid-enriched tailings;

feeding the bitumen froth to a Paraffinic Froth Treatment (PFT) operation to produce multiple PFT process streams including a bitumen product stream; and controlling alkaline agent dosage in the PSV, comprising:
acquiring near infrared (NIR) spectral measurements from an NIR probe located online in at least one of the multiple PFT process streams;

determining a concentration of a residual metal in the at least one PFT process stream based on the acquired NIR spectral measurements;

comparing the determined concentration of residual metal to a concentration specification; and adjusting the alkaline agent dosage for the PSV in response to a difference between the determined concentration of residual metal and the concentration specification.

In another aspect, there is provided a process for producing bitumen, comprising:

separating an oil sands slurry in a primary extraction operation to produce a bitumen froth and solid-enriched tailings;

feeding the bitumen froth to a Paraffinic Froth Treatment (PFT) operation to produce multiple PFT process streams including a bitumen product stream; and monitoring quality of the bitumen product stream produced by the PFT operation, comprising:

acquiring NIR spectral measurements from an NIR probe located online in a diluted bitumen overflow stream and/or the bitumen product stream of the PFT operation; and determining a concentration of at least one of vanadium and nickel based on the acquired NIR spectral measurements, wherein the vanadium and nickel are associated with asphaltenes and resins present in the bitumen within the diluted bitumen overflow stream and/or the bitumen product stream, and provide a proxy for the quality of the bitumen product stream.

In yet another aspect, there is provided a process for producing bitumen comprising:

separating an oil sands slurry in a Primary Separation Vessel (PSV) to produce a bitumen froth and solid-enriched tailings;

feeding the bitumen froth to a bitumen froth treatment operation to recover a diluted bitumen overflow in a froth separation unit and further produce bitumen in a solvent separation unit that recovers solvent from the diluted bitumen overflow; and controlling the bitumen froth treatment operation, comprising:

acquiring NIR spectral measurements from an NIR probe located online in at least one of the diluted bitumen overflow and the bitumen;

determining a concentration of at least one of vanadium and nickel based on the acquired NIR spectral measurements;

comparing the determined concentration to a concentration specification; and controlling a quality of the bitumen in response to a difference between the determined concentration and the concentration specification.

DETAILED DESCRIPTION

The techniques described herein relate to methods of monitoring various aspects of paraffinic froth treatment (PFT) operations. For example, the use of near infrared (NIR) spectrometry and chemometric analysis to continuously monitor and enable measurements of physical and chemical properties of various streams in PFT operations, notably of residual metals—such as iron (Fe), nickel (Ni) vanadium (V), calcium (Ca) and magnesium (Mg)—can be done in real time online and can facilitate process and quality control. In addition, NIR spectrometry can be used to acquire NIR spectra measurements from a PFT process stream and the NIR spectra measurements and chemometric analysis can, in turn, be used to determine composition characteristics of the PFT process stream. NIR spectrometry can also be used to determine other parameters, such as temperature, of PFT process streams. The determined concentration of residual metal or other parameters can, in turn, be used for process control that can include upstream adjustment of caustic addition in a primary separation vessel (PSV) as well as regulation of the PFT operations, such as solvent addition and asphaltene rejection.

Figure 1:
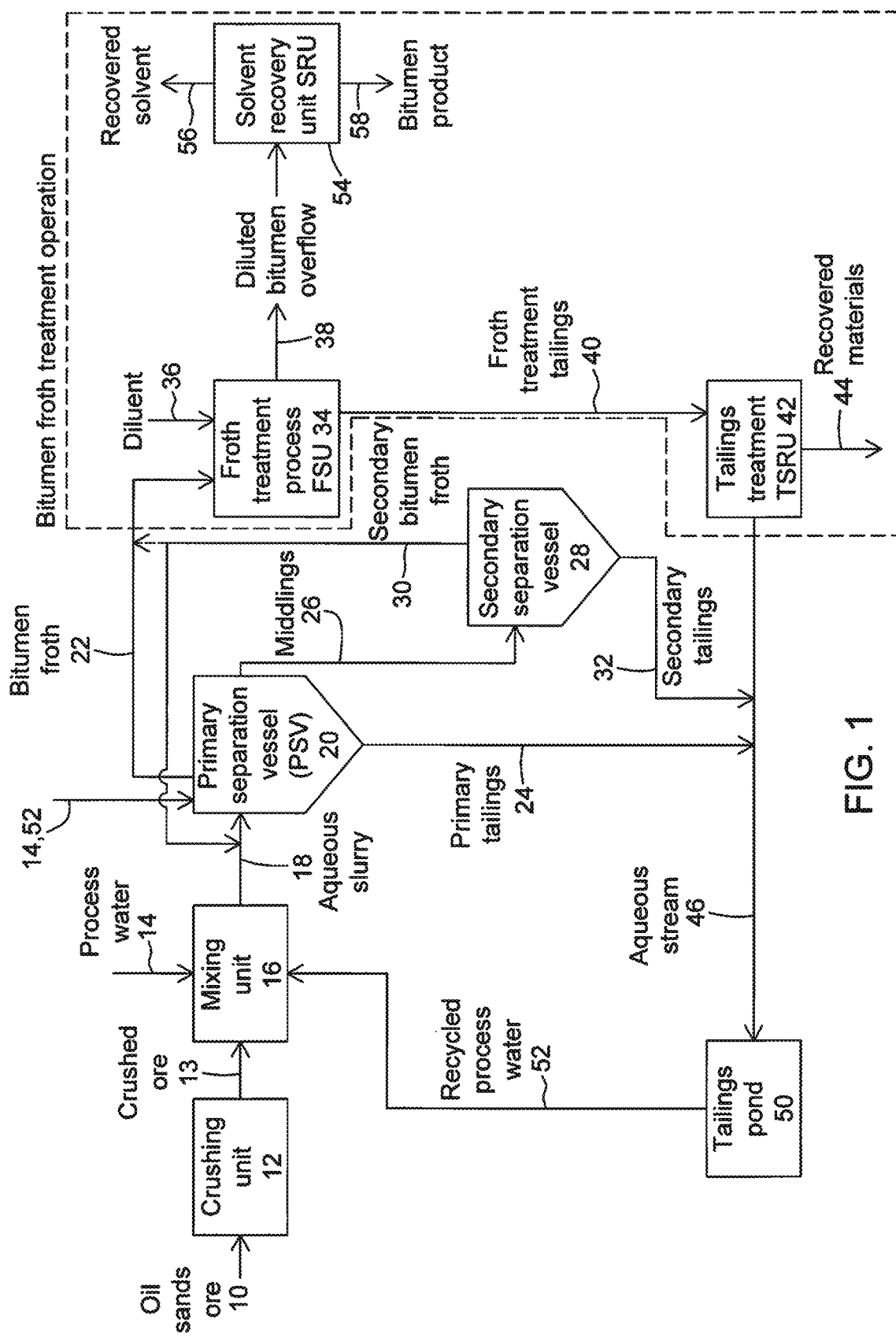
FIG. 1 is a process flow diagram showing a primary extraction operation and a bitumen froth treatment operation.

With reference to FIG. 1, a general example process for bitumen production using surface mining will be described. In a bitumen extraction operation, oil sands ore 10 is mined and crushed in a crushing unit 12 to obtain a crushed ore 13. The crushed ore 13 is then mixed with process water 14 (e.g., warm or hot water) in a mixing unit 16 to remove oversized clumps and form an aerated aqueous oil sands slurry 18. The mixing unit 16 can be for instance a rotary breaker that breaks up lumps of oil sands into smaller sized particles. The process water 14 and the sized oil sands material form the aqueous oil sands slurry 18, which can generally include between 5 wt % and 15 wt % bitumen, about 80 wt % solids, and between about 5 wt % and 15 wt % water.

The aqueous slurry 18 can then be shear conditioned to prepare the slurry for extraction of the bitumen from the solid minerals and water. The conditioning of the aqueous slurry 18 is typically performed through hydrotransport via a pipeline, which facilitates increased mixing, aeration and breakdown of lumps of oil sands ore in preparation for bitumen separation.

The aqueous slurry 18, which can optionally be further diluted with process water 14, is transported to a primary separation vessel (PSV) 20, which can also be referred to as a primary separation cell, "sep cell", or gravity separation cell. The PSV typically uses flotation and gravity mechanisms to separate bitumen from coarse sand and other solid particles. In the primary separation process, bitumen in the aqueous slurry 18 detaches from solid particles and attaches to air bubbles that are injected into the PSV 20, thereby allowing bitumen droplets to rise and float to the top of the PSV 20, forming the primary bitumen froth 22 that is recovered typically as an overflow stream. Coarse particles contained in the aqueous slurry 18 are relatively heavy and tend to sink to the bottom of the PSV 20. The portion of the aqueous slurry 18 that is not heavy enough to sink to the bottom of the PSV 20 but not light enough to float tends to remain in the middle of the PSV 20, and can be referred to as middlings 26. The aqueous slurry 18 is thus separated into three streams withdrawn from the PSV: a primary tailings underflow stream 24 (also referred to as coarse tailings), a middlings stream 26, and a bitumen froth overflow stream 22.

In some implementations, the middlings 26 can be sent to a secondary separation vessel 28 to be separated into secondary bitumen froth 30 and secondary tailings 32 (which can also be referred to as a fine tailings stream herein as they contain higher fines content compared to the coarse tailings). As shown in FIG. 1, the secondary bitumen froth 30 can be fed back to the primary separation vessel 20. Alternatively, the secondary bitumen froth 30 can be added directly to the primary bitumen froth 22. It is also noted that there may be additional separation vessels downstream of the secondary separation vessel 28, which further enable separation of residual bitumen from the water and mineral solids.

Still referring to FIG. 1, bitumen froth 22 typically includes about 60 wt % bitumen, about 30 wt % water, and about 10 wt % solid materials although these percentages can vary depending on various factors. The solid materials in the bitumen froth 22 typically include hydrophilic mineral materials and heavy minerals which can include adsorbed insoluble organic material.

The primary tailings 24 and secondary tailings 32 generally include between about 45 wt % and about 55 wt % solid materials, between about 45 wt % and about 55 wt % water, and residual bitumen (typically between about 1 wt % and about 3 wt % bitumen). The solid materials in the primary and secondary tailings 24, 32 are mainly sand and other fine hydrophilic mineral materials. The primary tailings 24 and secondary tailings 32 can then be disposed of in a tailings pond 50 or further treated to extract bitumen.

The bitumen froth 22 is further treated in a bitumen froth treatment operation that including several units. Bitumen froth 22 is first sent to a froth treatment process 34, also referred to as a froth separation unit (FSU), in which the bitumen froth 22 is diluted with solvent 36 to obtain a solvent diluted bitumen froth. The solvent 36 is a paraffinic solvent, which can for example include C4 to C8 aliphatic compounds and/or certain natural gas condensates. Pentane is one solvent that has been used in PFT operations. The paraffinic solvent is used under conditions such that when added to the bitumen froth it induces precipitation of asphaltene aggregates that contain asphaltenes, water and fine mineral solids. Higher solvent-to-bitumen ratios tend to lead to higher levels of asphaltene precipitation from the bitumen.

Still referring to FIG. 1, the diluted bitumen froth is separated in the FSU 34 into a diluted bitumen overflow 38 and froth treatment tailings 40 including solid materials (hydrophilic mineral materials, heavy minerals and insoluble organic materials), water, residual diluent and residual bitumen. The diluted bitumen overflow 38 can be sent to a solvent recovery unit (SRU) 54, which produces two streams as recovered solvent 56 and bitumen product 58. The FSU itself can include two or three settler vessels that are arranged in a counter-current configuration (not illustrated in FIG. 1).

In some implementations, froth treatment tailings 40 are treated in an oil sands tailings treatment process 42, which may employ a tailings solvent recovery unit (TSRU), in order to separate the froth treatment tailings 40 into various recovered materials 44 such as solvent and/or bitumen, and an aqueous stream 46, also referred to as TRSU tailings, including process water, heavy minerals, and/or hydrophilic mineral materials. The TSRU tailings 46 including process water and hydrophilic mineral materials can be disposed of in a tailings pond 50 for settling.

In the implementation shown in FIG. 1, the coarse tailings stream 24 and the fine tailings stream 32 are added to the TRSU tailings 46 for disposal in the tailings pond 50.

Still referring to FIG. 1, an overlying water phase can be pumped out of the tailings pond 50 and re-used as recycled process water 52 in the mixing unit 16 to obtain the aqueous slurry 18, as well as in various other applications within the oil sands processing facility.

One or more alkaline agents, such as caustic soda (NaOH), sodium silicate, sodium bicarbonate, sodium phosphate and the like, can be added directly to the aqueous slurry 18, before starting primary separation in the PSV, to chemically condition and prepare the aqueous slurry for bitumen extraction and separation in the PSV. An alkaline agent can be added to the process water 14, to the mixing unit 16, to the aqueous slurry before, during or after hydrotransport, and/or can be added directly into the PSV 20. Dosing of the added alkaline agent can impact the content of certain residual metals which are present in certain downstream materials, such as the bitumen product 58. Metals content can influence bitumen quality and can also be an indicator of upstream processing characteristics.

For instance, when adding caustic soda for the PSV, ions exchange between $Na^+$ and $Ca^{2+}$, leading to the formation of calcium naphthenates with the naturally occurring naphthenic acids in the oil sands. Calcium naphthenates can be undesirable and lower bitumen quality. Elevated caustic soda levels can also lead to additional $Ca^{2+}$ in the bitumen froth and can lead to the emulsification of bitumen and smaller bitumen droplets, which can impair bitumen recovery.

It should be noted that "PFT process stream" means herein any fluid stream involved in the PFT operation. PFT process streams can therefore include bitumen froth, diluted bitumen froth, diluted bitumen overflow from FSU, first or second stage overflow streams in the FSU, first or second stage underflow streams in FSU (when two-stage FSU is used), recovered solvent from the SRU and TSRU, bitumen product from the SRU, TSRU tailings and diesel-containing streams used for start-up or cleaning the PFT vessels or lines. The PFT process stream may be characterized as a two-phase fluid containing a hydrocarbon phase and an aqueous phase, or a single-phase fluid in some cases.

It should be noted that a "residual metal" as discussed herein refers to a metal, an alkaline earth metal or a metalloid that is present in the PFT process streams. Metals can be found in process water and the oil sands ore used to prepare the oil sands slurry, such that residual metals are present in PFT process streams. More particularly, residual metals can include native materials present in the ore, including metals such as aluminum (Al), iron (Fe), nickel (Ni) and vanadium (V); metalloids such as silicon (Si); and alkaline earth metals such as calcium (Ca) and magnesium (Mg). Different metals have different characteristics and can provide different indications and insights regarding bitumen quality and upstream processing performance. Metal concentrations can also be useful proxies of other properties, for example when a metal is associated with certain sub-components of the bitumen.

In addition, process water chemistry can evolve over time, from the moment a plant is put into operation and fresh water is used initially and in start-up processes, to many years later when processes have reached an equilibrium in terms of recycled process water that has gone through multiple cycles of separation processes. As seen in FIG. 1, water from the tailings pond 50 can be reused as process water 52 to mix with the oil sands ore 13 and produce the oil sands slurry 18. This recycled process water can have a different water chemistry compared to fresh water. After a certain number of years of a plant's operation, i.e., once the plant could be said to be "mature", process water chemistry can reach an equilibrium stage. In contrast to a mature plant, water chemistry of process water used at a newer plant can change substantially in the first few years of operation, in particular with regard to the residual metals, which can play a relevant role in helping to determine bitumen quality and to determine dosage of process-aids in primary extraction operations and froth treatment operations.

It follows that as a plant is transitioning from a start-up or early mode using mainly fresh water having low concentrations of certain residual metals, to a mature mode using process water having higher residual metals concentrations, monitoring the contents of residual metals in various froth treatment streams can be useful to characterize bitumen quality and control process-aids dosage, such as alkaline agent addition in primary extraction operation.

In addition, online/inline NIR measurements can facilitate rapid data acquisition of process variables that are relevant to the control of PFT process stream quality. NIR monitoring can indeed be performed online/inline to reduce turnaround time if the residual metals in the bitumen product become off-specification, and enable adjusting operational conditions to control bitumen product quality. Reliable online/inline measurement can replace manual sampling, reduce human errors related to laboratory analysis, and minimize safety risks associated with sample collection. As such, NIR based techniques are a powerful tool for implementation of online/inline bitumen product quality control and for online/inline operational control based on monitored residual metal contents. In addition, once calibration models have been developed, the NIR based data acquisition can enable rapid determining of multiple variables from a single NIR probe in a PFT process stream (e.g., metals concentration, other compositional characteristics, temperature, and other properties of the given fluid).

Monitoring the contents of residual metals in froth treatment streams can be challenging as the contents of residual metals can vary from the start-up mode to the mature mode, or following the addition of a certain process-aid in a particular part of the process or a particular froth treatment stream. For example, the calcium concentration can be up to 200 ppm in bitumen product when caustic soda is added in primary extraction, whereas the calcium concentration can be below 10 ppm in the bitumen product when the slurry is untreated by caustic soda. In addition, some residual metals contents can remain substantially within the same range in start-up or mature mode. For example, nickel concentration in the bitumen product can be between 50 ppm and 60 ppm in start-up mode and mature mode when the asphaltene content in the bitumen product is about 10 wt %. Thus, depending on the type of metal that is monitored and the stage or maturity of the extraction operation, changes in metals concentration can provide valuable information for an operator.

Process Control Based on Monitoring of Residual Metals

Residual metal concentrations may be monitored continuously and online, thereby facilitating real-time detection of off-specification compositions of PFT process streams in order to facilitate PFT process control and bitumen quality control.

In some scenarios, bitumen, solids, water or asphaltenes contents in a PFT process stream can remain relatively constant while the residual metal concentrations can vary. Thus, basing process control techniques on residual metal concentration as one of the input variables can lead to enhanced performance, particularly for variable oil sands slurry compositions and evolving maturity of the PFT operation.

Figure 18:
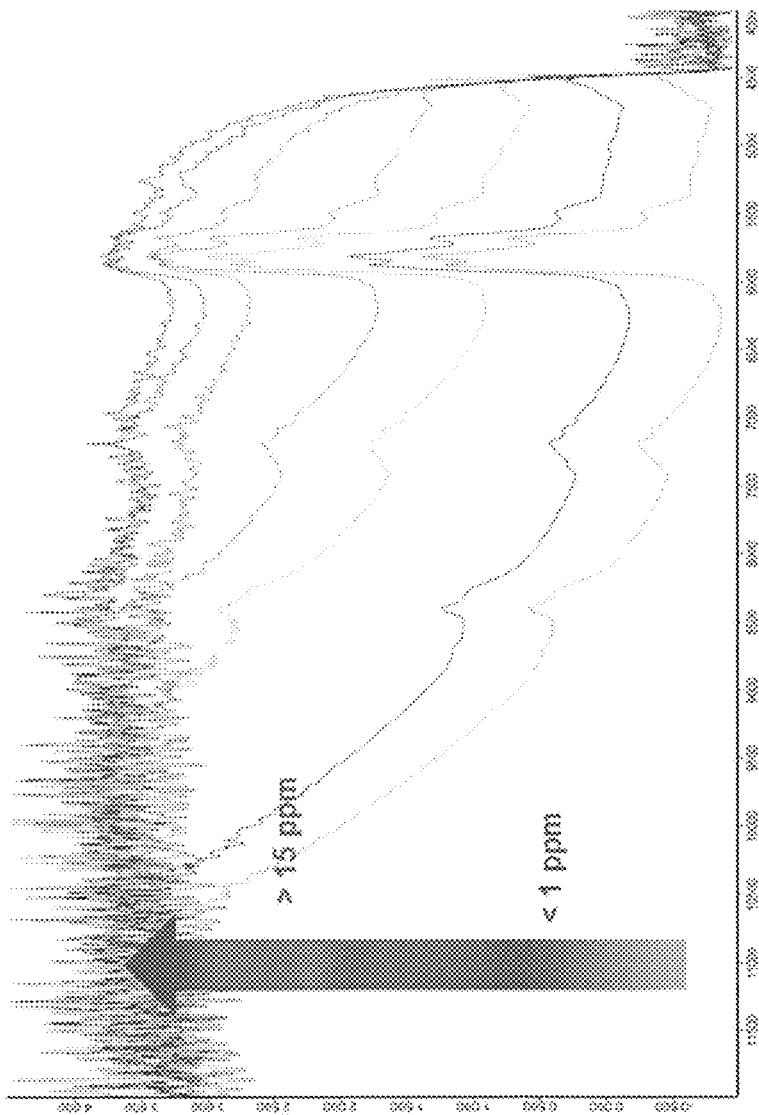
FIG. 18 is a graph of NIR spectra of diluted bitumen overflow versus chloride in diluted bitumen overflow.

In some implementations, NIR based monitoring of the residual metals iron, sodium, calcium, magnesium, nickel and/or vanadium in PFT process streams can be used to control extraction of the bitumen from the oil sands slurry in upstream primary extraction operations, such as in the PSV. Elements associated with metals, such as chloride, can also be monitored with NIR techniques as seen on FIG. 18.

For example, in the context of PSV operations, caustic soda is typically added to an oil sands slurry with higher fines or clay contents so that the hydroxyl ions can attach to positively charged fine particulate mineral solids and inhibit attachment to the bitumen droplets. This leaves the hydrophobic bitumen free to attach to air bubbles, thereby improving bitumen recovery. Addition of surfactants, and other additives can also be performed to change physicochemical interactions between components of the oil sands slurry to facilitate bitumen extraction.

Monitoring the calcium concentration in a PFT process stream can enable detection of increases in the calcium concentration, which can be an indicator that elevated caustic addition has occurred upstream in the PSV. In some cases, the caustic addition could be adjusted (e.g., lowered) in response to the NIR-based monitoring of the calcium concentration. In addition, the caustic dosage could be maintained while adjusting other operating conditions of the PSV in order to enable a reduction in the calcium content in downstream PFT process streams.

In terms of PFT process control, there may be a controller or associated equipment that receives the NIR-derived process data and adjusts at least one upstream or downstream process parameter. The control can be feedback or feedforward. In the implementation where the NIR-derived process data is obtained for determining calcium concentration in the diluted bitumen overflow, the PFT process control can include changing caustic soda for an alternative alkaline agent that is added to the oil sands slurry, altering the composition of the alkaline agents or general process aids added to the slurry, adjusting the amount of added caustic soda, or controlling the flow rate of dilution water that is added to the oil sands slurry before being fed into the PSV, thereby adjusting a calcium content of the monitored PFT process stream.

In some other implementations, NIR based monitoring of the residual metals nickel and/or vanadium in PFT process streams can be used to monitor or assess bitumen product quality since these metals can be associated with asphaltenes and resins present in certain PFT streams.

For instance, in PFT operations, the addition of a paraffinic solvent (e.g., $C_5$ alkanes such as n-pentane and isopentane) to the bitumen froth induces the precipitation of asphaltene flocs or aggregates. The composition and behaviour of the resulting fluids can be relatively complex and challenging to handle. The target asphaltene content in the diluted bitumen overflow stream can be less than 10 wt %, in order to provide certain quality targets for downstream processing and handling. NIR based monitoring of nickel and vanadium in the diluted bitumen overflow can be used to determine asphaltene content and control addition of the paraffinic solvent if needed. NIR monitoring can be done in the overflow line through which the dilute bitumen flows and/or within one or more zones of the settling vessel such as an upper zone that feeds the overflow outlet receiving the diluted bitumen. By determining nickel and/or vanadium concentrations of the diluted bitumen, early detection of elevated levels can be achieved compared to measuring the final bitumen product further downstream.

Figure 5:
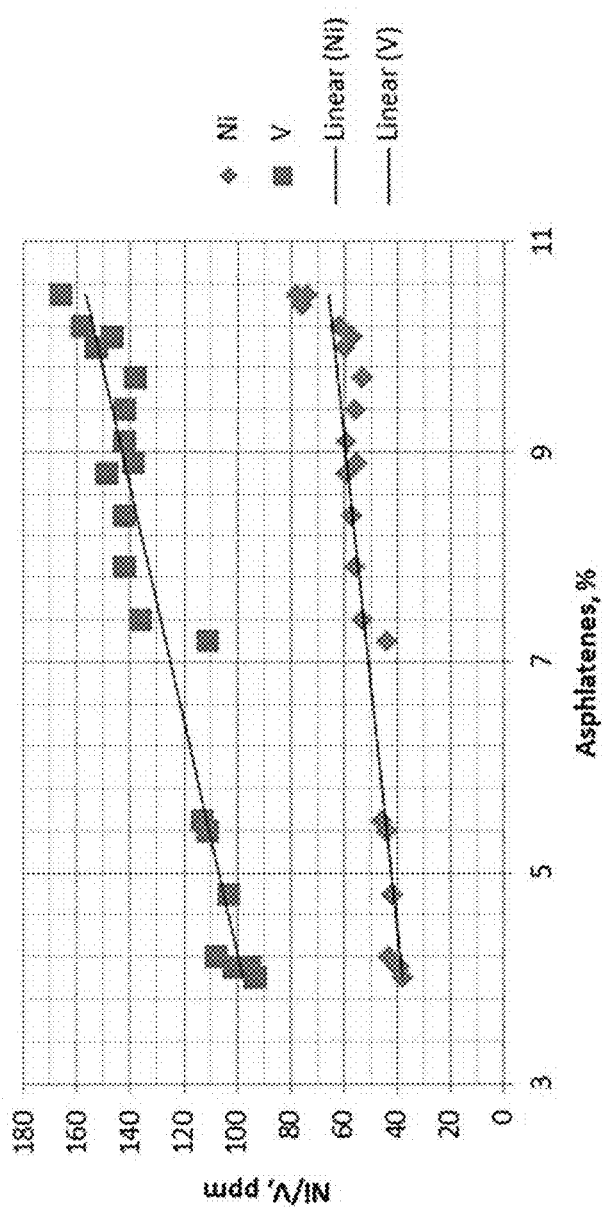
Figure 17:
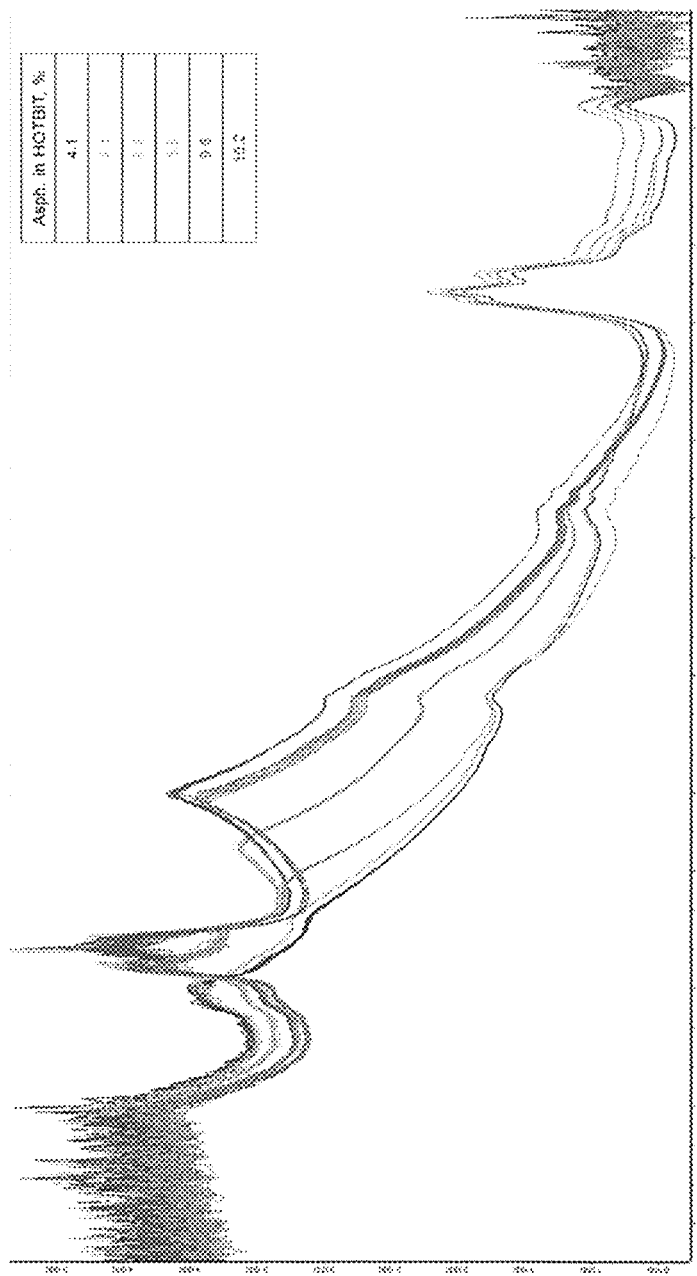
FIG. 17 is a graph of NIR spectra of diluted bitumen overflow versus asphaltene content in diluted bitumen overflow.

It has been found that the NIR spectra of diluted bitumen overflow show different patterns with the asphaltene content in bitumen for example, and as shown in FIG. 17. Therefore, according to the pattern change of NIR spectra, the asphaltenes content can be approximated and monitored. For example, FIG. 5 shows both nickel and vanadium concentrations (in ppm) in bitumen product as a function of the asphaltenes content measured by NIR. The profile of nickel and vanadium concentration in bitumen product can thus track bitumen product quality in terms of asphaltene content, for example.

Controlling the PFT process may therefore be performed to maintain or increase the quality of the diluted bitumen. As the quality of the bitumen can be characterized by the concentration in nickel and vanadium, once these concentrations are determined using NIR measurements and NIR correlation models, operational conditions may be adjusted to keep the metal contents within predetermined quality specifications. For example, if nickel and vanadium concentrations are off specification, controlling the PFT process can include increasing asphaltene rejection, which could be achieved by increasing solvent addition and solvent-to-bitumen ratio in the bitumen froth prior to separation.

It has been found that online monitoring of residual metal concentrations in PFT process streams, alone or in combination with various other physicochemical parameters, can be performed via NIR based measurement. Such monitored concentrations can be relayed to a control unit which can detect off-specification situations in the monitored PFT process streams. Residual metal concentrations in PFT process stream can also be influenced by primary extraction conditions. Therefore, online detection of off-specification concentrations in residual metals in PFT operations can facilitate to adjust in real time operation of the primary extraction and reduce losses in off-specification bitumen product.

Figure 2:
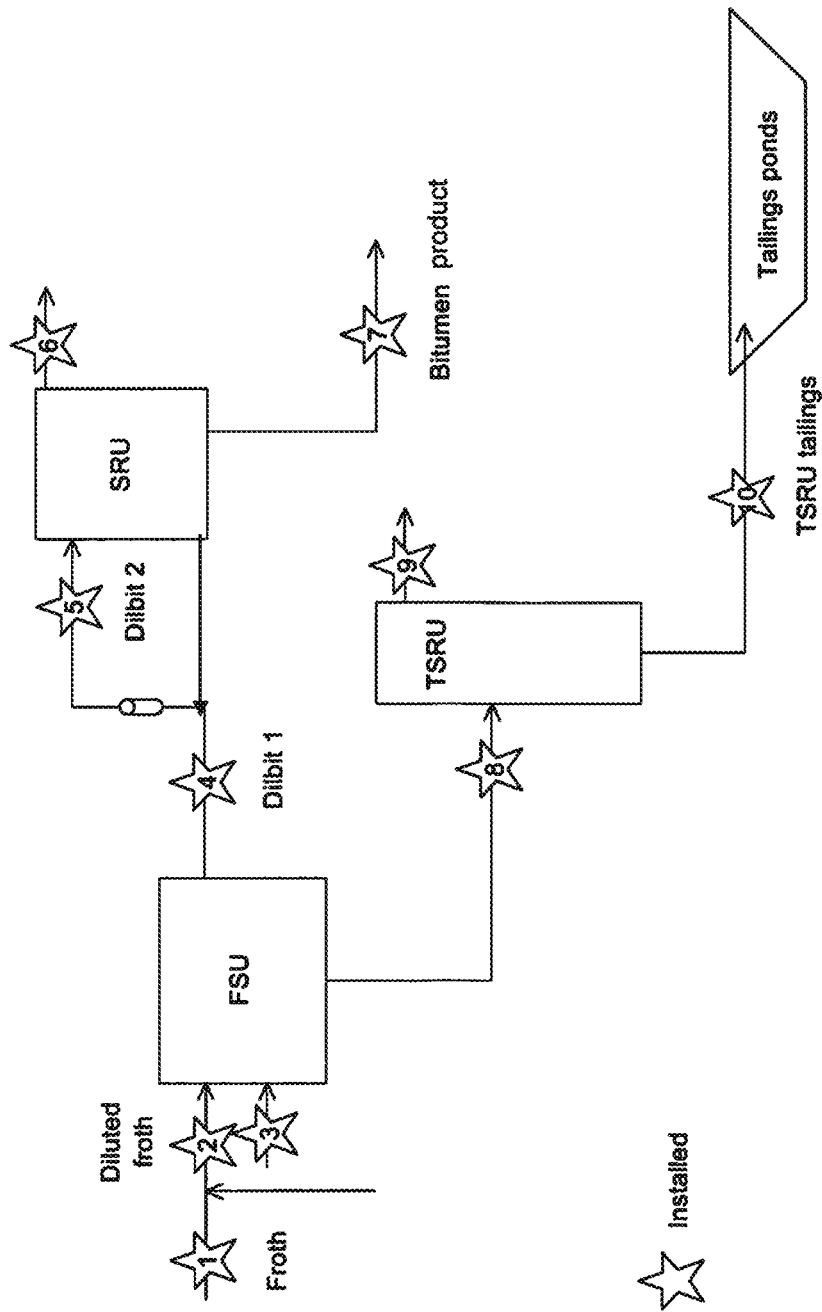
FIG. 2 is a schematic illustrating a PFT operation including NIR-based monitoring of PFT process streams.

Referring to FIG. 2, several NIR probes can be provided at various locations of the PFT operation to simultaneously measure multiple physical and chemical parameters of the PFT process streams and units. The particular streams that are selected for detecting residual metals using NIR probes can facilitate monitoring relevant features of those streams to enhance overall monitoring and quality control. For example, a first NIR probe 4 can be provided to determine at least residual metal contents in a diluted bitumen overflow stream produced by the FSU and supplied to the SRU. A second NIR probe 7 can also be provided to determine at least residual metal contents of the bitumen product from the SRU. Other locations can benefit from the placement of NIR probes as seen on FIG. 2. The NIR derived process data related to residual metal concentrations can therefore be one input parameters provided to the controller, although additional variables can also be measured and provided to enhance the control strategy, as detailed in below Table 1.

TABLE 1

Physical and chemical parameters measured by online NIR analyzers in PFT

| NIR Application | PFT Unit Parameters | FSU OF | FSU Feed | SRU Feed | SRU Product | TRSU Tailings |
|---|---|---|---|---|---|---|
| Chemical property | Bitumen | ✓ | ✓ | ✓ | ✓ | ✓ |
| | Solvent | ✓ | ✓ | ✓ | ✓ | ✓ |
| | Water | ✓ | ✓ | ✓ | ✓ | N.A |
| | Solids | ✓ | ✓ | ✓ | ✓ | -N.A |
| | Asphaltenes, naphthenic acids, TAN | ✓ | ✓ | ✓ | ✓ | ✓ |
| | Ni, V, Ca, Mg Fe, Al, Si | ✓ | N.A | | ✓ | — |
| | Process aids | ✓ | | | ✓ | |
| Physical property | Density | ✓ | N.A | ✓ | ✓ | N.A |
| | Temperature | ✓ | | ✓ | ✓ | |
| | Pressure | ✓ | | ✓ | ✓ | |
| | Viscosity | ✓ | | ✓ | ✓ | |
| | Flow rate | ✓ | | ✓ | ✓ | |

Thus, the controller can be configured as a multi-parameter control system which receives multiple input variables and controls multiple aspects of the primary extraction operation and of the PFT operation. The multiple variables may be different NIR-based measurements taken from one or more different streams or locations in the facility. Also, multiple NIR-based measurements of the same parameter for different PFT process streams can facilitate redundancy and higher accuracy for the process control techniques described herein.

It is also noted that each NIR probe in a given PFT process stream can acquire spectra data that can then be used with multiple pre-determined calibration models to determine respective multiple variables. This may be done within a monitoring system that generates multiple values to indicate properties of the PFT process stream under monitoring. For example, referring to FIG. 2, for the diluted bitumen stream, probe 4 can be configured to obtain spectra data that are used to derive bitumen content, solvent content, asphaltenes content, water content, density, solids content, temperature, as well as one or more residual metals contents. In this manner, each probe can obtain compositional variables, such as residual metals contents, fluid temperatures, and/or other variables relevant to the given process streams. In FIG. 2, probe 5 can be configured to obtain the same information as probe 4 to provide enhanced accuracy and redundancy. In addition, different frequency ranges of each given spectra can be used as the spectra input to different models to obtain different property values.

NIR Spectrometry Implementations

In some implementations, NIR probes are used to obtain NIR spectral data that can be used to monitor PFT process stream compositions as well as operating parameters of PFT units. The NIR probes and associated analyzers and controllers can be automated to provide continuous data acquisition and control, or can be manual or semi-manual to provide more periodic data acquisition and control. The NIR probes can be installed to provide NIR online or at-line measurements. The NIR probes can be used online, where the probes are physically integrated on pipes located upstream or downstream any unit of the PFT operation or with respect to slip streams. The NIR probes can also be integrated within one or more vessels.

Transmission-type NIR probes (transmission probes) and/or reflectance-type NIR probes (reflectance probes) can be used It was found that reflectance-type NIR probes provided sharp, clear, stable spectra which can be used for FSU feed and TSRU streams; while transmission probes were sensitive and used in diluted bitumen overflow, SRU feed and bitumen product. It should be noted that the two different types of NIR probes may be used for different applications within PFT, e.g., for different concentration ranges. In some implementations, a transmission probe can be selected to measure concentrations lower than 1000 ppm (e.g., for residual metals). A reflectance probe, which is more robust and easier to maintain but less sensitive, can be selected to measure concentrations above 1000 ppm. In some implementations, one or both types of probes may be present in a PFT operation. For example, a reflectance probe may be present to detect a high concentration corresponding to a safety or upset limit, while a transmission probe may be present to detect lower operational concentrations that may be expected during normal operation (e.g., for fine-tuning).

For instance, calcium content in diluted bitumen overflow from FSU can be too low, e.g., between 5 and 10 ppm, to be accurately measured with reflectance NIR, and a transmission probe would be preferred in such cases. Transmission and reflectance probes can be located at different points in the PFT operation to monitor different streams, or both transmission and reflectance probes can be located at the same point and optionally integrated within the same probe structure for online implementation. It is also noted that a secondary probe that uses other measurement techniques can be used to measure certain variables at very low levels.

The term "NIR measurements" as used herein, encompasses spectral measurements such as NIR spectra. Depending on the type of probe used, i.e. reflectance probe or transmission probe, NIR spectra may be reflectance spectra or transmission spectra. In some implementations, the NIR spectral measurements include at least one NIR spectrum. It may include a plurality of NIR spectra; in such scenarios, the NIR measurements may comprise an average NIR spectrum derived from the plurality of NIR spectra.

In some implementations, NIR spectral measurements of a PFT process stream can be acquired by positioning the NIR probe within a pipe section through which a two-phase PFT process stream flows. In particular, the pipe section is selected and the NIR probe is positioned within the pipe section to be in contact with a stratified hydrocarbon phase of the PFT process stream, thereby not being in contact with or acquiring spectral data from the aqueous phase. The radiation source is directed at the hydrocarbon phase and the detector receives the NIR radiation from the hydrocarbon phase.

PFT process streams include hydrocarbon, mineral and aqueous components, which may tend to stratify inline under certain circumstances. Within the overall PFT system, there can be various equipment, instrumentation and piping configurations that may promote stratification or mixing of the two phases at different points in the process. Valves, pipe bends, mixers, and the like tend to cause the two phases to mix together, while straight horizontal pipe sections can promote stratification of the hydrocarbon phase and the aqueous phase to respectively form upper and lower strata within the pipe section.

In some implementations, the NIR probe is installed online in a pipe section at sufficient distance after a flow impediment (e.g., valve, vessel or pipe bend), where the two phases (hydrocarbon and aqueous) are stratified. The NIR probe location and orientation is provided to ensure that it is analyzing the hydrocarbon phase. In some implementations, the NIR probe can be oriented toward the hydrocarbon phase to minimize or avoid exposure to the water phase. The radiation source emitted by the probe is directed toward the hydrocarbon phase of the PFT process stream.

In some implementations, the NIR probe is installed in straight horizontal pipe section where the PFT process stream is stratified. In some implementations, the NIR probe is installed in a horizontal pipe section spaced away from elbows, valves or vertical sections where the flow regime would cause mixing and destratification of the phases.

In some implementations, the NIR probe locations can be based on CFD modelling regarding the separation of immiscible systems, mathematical models, and/or empirical testing. CFD models, for example, can help understand how immiscible systems flow in pipes. For instance, it has been found that for large size lines and high velocities in the line, the flow tends to be stratified in the horizontal direction. According to tests, it was found that separate layers formed at 6 to 8 pipe diameters downstream from a turbulence point in the pipeline. This behavior allows placing the probe in the upper region of the pipe section to ensure that the probe stays within the hydrocarbon phase which is lighter than the aqueous phase. In some implementations, the NIR probes that are placed in-line can be located at least 6, 7, 8, 9 or 10 pipe diameters downstream of a turbulence point.

In terms of the NIR probe location within the cross-section of a pipeline, it can be useful to consider the pipe's circular cross-section which has an upper region and a lower region separated by a horizontal chord. The upper and lower regions can be defined depending on the composition of the PFT process stream and the degree of stratification, for example. Locations around the pipe's cross-section will be described using a clock position analogy below.

In some implementations, the 12 o'clock position is avoided since non-condensable vapors that may be present can be at the top of the pipe and could thus interfere with the NIR probe. In a preferred implementation, the NIR probe is installed close to the inner pipe wall between the 10 o'clock and the 11 o'clock position (or the 1 o'clock and 2 o'clock position).

The position of the NIR probe can depend on the volumetric proportions between the immiscible phases within the pipe section. In some implementations, the PFT process stream is a diluted bitumen overflow stream, which is substantially only hydrocarbon phase (generally at least 98%) and thus the aqueous phase is minor. In such implementations, the NIR probe may be placed in a position chosen over a larger surface of the pipe, e.g., between the 7 o'clock position and the 5 o'clock position avoiding region around the 6 o'clock position as well as the 12 o'clock position as mentioned above. Nevertheless, since breakthroughs of the aqueous phase into the hydrocarbon phase due to high flux may occur, the NIR probe can be generally installed at the 9 o'clock position or above.

In some implementations, the NIR probe can be installed on a sample bypass loop or slip stream line. The NIR probe can thus be isolated from the operational unit and pipeline, which can facilitate removal, maintenance and/or troubleshooting of the probe, if required, while the PFT process unit is online. For example, for removal or maintenance, the bypass or slip stream line can be shut off and the PFT operation can continue uninterrupted. The bypass or slip stream line can also be configured so that the NIR probe is installed at a desired cross-sectional location (e.g., around 11 o'clock) and a desired longitudinal location (e.g., at least 6 pipe diameters downstream from a turbulence point) to acquire the measurements of interest. Providing NIR probes associated with bypass or slip stream lines can also facilitate adjusting sample conditions and cleaning (e.g., flushing) of the NIR probe for instance by flushing the sample line instead of the process line to prevent plugging and/or fouling of the probes.

The NIR measurements that are obtained are used to construct NIR correlation models, determine various physicochemical characteristics of PFT process streams including residual metals contents, and ensure quality control or operational control of the PFT operation.

Determination of Physicochemical Characteristics Based on NIR Monitoring

Physicochemical characteristics, including contents of residual metals such as Al, Fe, Ni, V, Si, Ca and Mg, can be determined using a NIR calibration models having a correlation allowing for accurate estimation of the characteristics, and the measurements can be used for process control strategies to maintain performance and efficiency.

Chemometrics is a method used herein for developing NIR calibration models for chemical systems. Chemometric methods facilitate processing laboratory or other data along with NIR spectral measurements to provide a calibration baseline model (also called a preliminary model). In some implementations, chemometric methods are used to develop multivariable calibration models using appropriate statistical tools, such as OPUS/QUANT Spectroscopy Software (by Bruker™), for example. Therefore, reliable NIR monitoring of residual metals content in froth treatment process streams has been developed.

Final bitumen product in a PFT operation needs to meet quality specifications before being commercialized to refineries. Generally, bitumen product should contain less than 10 ppm of calcium. Compliance with these specifications may be enabled and/or controlled by monitoring residual metals in PFT process streams based on NIR spectrometry, and further control dosage of process-aids if needed.

For example, the contents of vanadium and nickel in the produced bitumen can be indicative of the asphaltene rejection. Indeed, nickel and vanadium are heavier metals which tend to be agglomerated with asphaltenes. In addition, nickel and vanadium are known to be poisonous to the catalyst used in refineries. Therefore, determination of the nickel and vanadium contents in the produced bitumen is indicative of the bitumen quality, and validates whether the bitumen meets the specifications of refineries.

Figure 19:
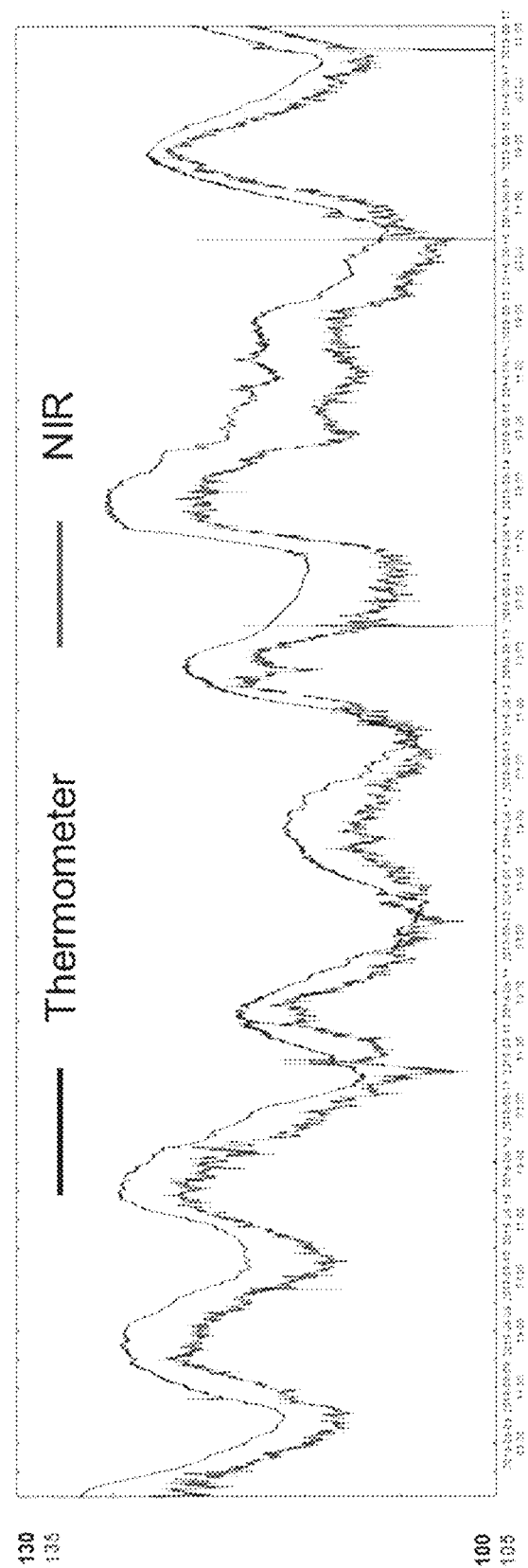
FIG. 19 is a graph showing comparative temperature values determined from online NIR-based measurements and from thermometer-based measurements in hot bitumen stream.

Physicochemical characteristics of the PFT process stream can also be a physical property, such as density, viscosity, temperature or vapor pressure. For example, temperature of hot bitumen strean in PFT operation can be determined based on NIR measurements as shown on FIG. 19.

Obtaining NIR spectral measurement can include the use of an NIR probe as described further above. In some implementations, at least one NIR probe is installed online, positioned in an upper region of a horizontal pipe section and within a hydrocarbon stratum; and a light source (e.g., laser beam) is emitted by the NIR probe into the PFT process stream. The probe may be a reflectance probe or a transmission probe, and can be selected depending on the nature of the PFT process stream and the characteristic to be determined.

The light emitted by the NIR probe interacts with the PFT process stream and the resulting radiation is captured by an NIR detector. The radiation received after interaction with the PFT process stream is captured and can be analysed by an NIR analyser, which provides the NIR spectral measurements. Any NIR analyser fitted with a fiber optic probe can be used to analyse the detected IR radiation and provide the NIR spectral measurements. For example, a Matrix-F FT-NIR spectrometer (Bruker®) with transmission and reflectance probes may be used to take NIR spectral measurements.

In some implementations, the NIR spectral measurements are continuously obtained during operation of the PFT process, and the physicochemical characteristics of interest are continuously determined. Once the NIR spectral measurements are obtained, they can be used to monitor the PFT process characteristics based on NIR calibration models. More regarding the calibration models will be discussed further below.

The NIR calibration models may be built using chemometric methods, laboratory analyses of collected or prepared samples, and corresponding NIR reflectance or transmission spectral measurements. In some implementations, the NIR calibration models are multivariable calibration models, and may be prepared using density QC/QA analysis. In addition, methods that include statistical tools, linear offset subtraction, straight line subtraction, vector normalization, min-max normalization, multiple scatter correction (MSC), first derivative and second derivative data processing methods, and/or a combination of data processing methods may be used, to emphasize chemical information derived from the NIR measurements and improve precision and accuracy of the determined characteristics.

The multi-functionality of an NIR probe and associated calibration models can facilitate monitoring of physical and chemical properties of various PFT streams as well as relevant parameters of PFT processing units. A series of NIR calibration models using chemometric methods and based on NIR spectra may be developed to determine the concentration of residual metals in the diluted bitumen overflow or in the bitumen product for instance.

In some implementations, the NIR model is a multivariable calibration model. The NIR spectra include overtones and combination bands of the fundamental molecular absorptions found in the mid infrared region. NIR spectra include generally overlapping vibrational bands that may appear non-specific and poorly resolved. Therefore, qualitative and quantitative NIR spectroscopic methods advantageously include the application of multivariate calibration algorithms and statistical methods to model NIR spectral response to chemical or physical properties of the samples used for calibration. In multivariate analysis, the entire spectrum is analyzed and the model distinguishes each component present based on the series of peaks, slopes, and shapes within the spectrum, rather than by analysis at a particular wavelength or narrow range for each component.

Figure 6:
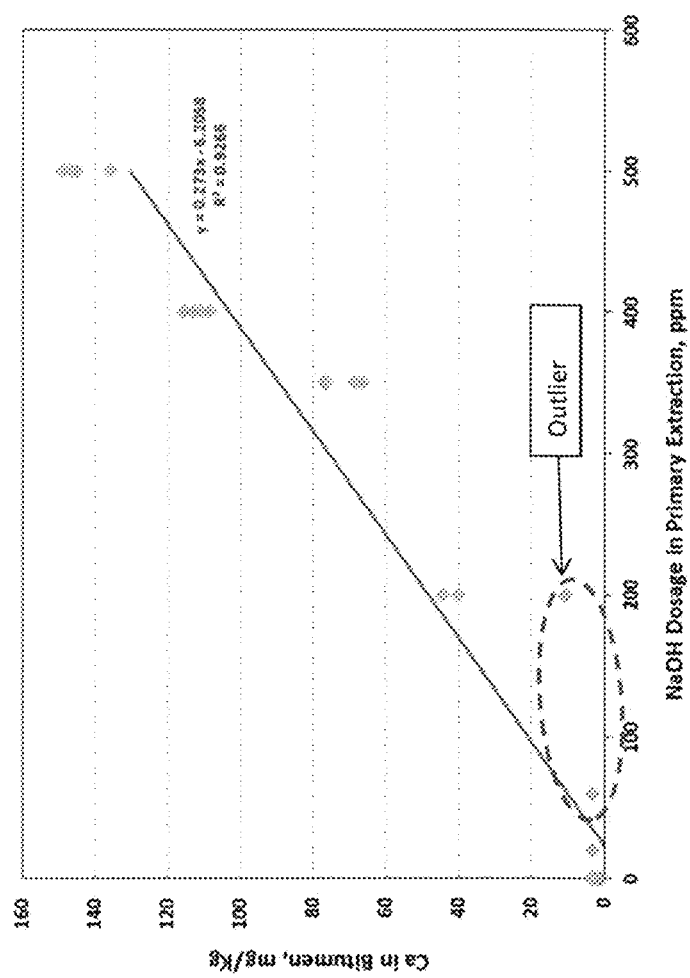
FIGS. 6 and 7 are graphs showing the correlation of calcium concentration in bitumen and caustic added in the primary extraction.

In terms of developing calibration models for residual metals, the NIR calibration model can correlate the NIR spectral measurements with the concentration of the relevant metals measured. The NIR calibration model can be developed by correlating NIR measurements with laboratory analyses. As illustrated in FIG. 6, the NIR model development can include certain steps, e.g., organizing NIR spectra; calibrating a baseline model; removing outliers identified in quality assurance/quality control (QA/QC) analyses; removing outliers identified by the NIR model and recalibrating; recording and analyzing outliers; and further improvement to the model. Various model development, refinement and validation techniques can be used.

In some implementations, NIR models can be developed by compiling laboratory analyses for the measurements of each individual metal concentration in the PFT process stream (e.g., diluted bitumen overflow) with NIR spectral measurements, using a chemometric method.

It was found that the incorporation of QA/QC laboratory data facilitated development of a reliable model. QA/QC analysis allows identifying and removing outlier data that may decrease the accuracy of the correlation model. The term "outlier data" refers to any observations that are distant from other observations in a random sample from a population, and may indicate measurement variability and/or experimental errors.

Multivariable correlation models facilitate developing accurate estimations of elements Fe, Ni, V, Ca, Na, Cl and Mg content as a function of NIR measurements. Correlation models may be improved based on different data processing methods. In some implementations, first derivative method, second derivative method, straight line substraction, vector normalization method, Multiple Scatter Correction (MSC) method, and/or a combination of these methods (as mentioned above) may be used.

An example of modeling processes is described in more detail in the Experimentation section further below.

NIR Based Determination of and Control for Alkaline Agent Addition in PSV

In some implementations, the process-aid is an alkaline agent added to the oil sands slurry in primary extraction operation. Primary extraction operation may be controlled to increase or decrease the dosage of alkaline agents such as caustic soda.

Figure 7:
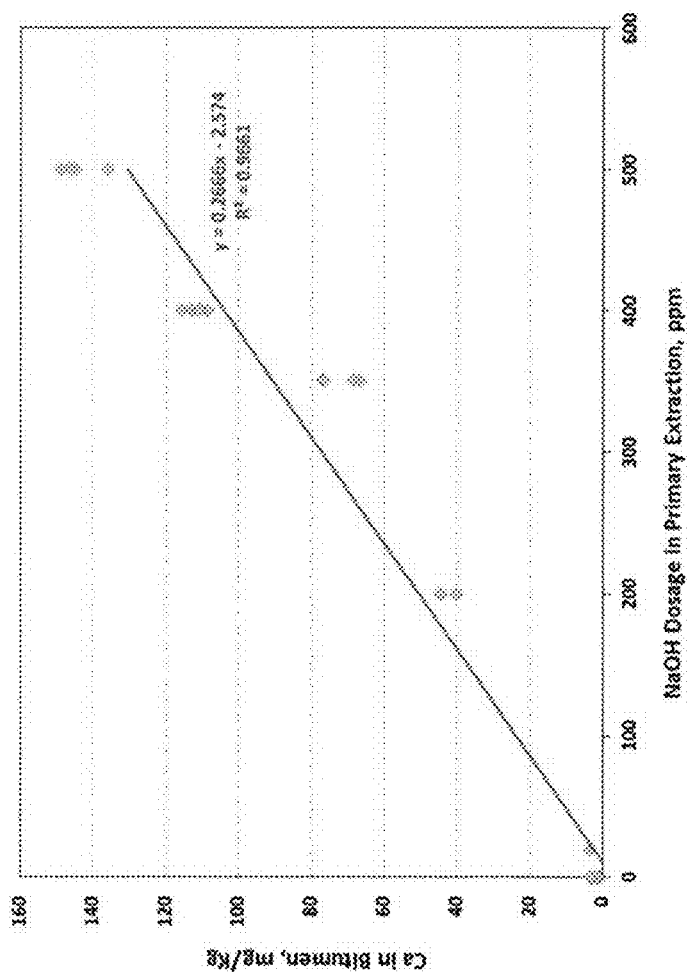

NIR spectra of diluted bitumen overflow can show different patterns with the upstream addition of caustic soda to the oil sands slurry for example. Therefore, according to the pattern change of NIR spectra, the presence and/or performance of the process-aid can be monitored. For example, FIGS. 6 and 7 shows calcium concentration (in ppm) in bitumen as a function of the dosage of caustic soda. The profile of calcium concentration in diluted bitumen overflow can thus track the best dosage of caustic soda, and prevent a caustic overdose which could reduce product quality for example.

Thus, in the PFT process, the process-aid dosage can be monitored using NIR techniques. One can thus obtain NIR spectral measurements as described herein, and determine a physicochemical characteristic of an overflow stream, which may be related to the process-aid dosage. The physicochemical characteristic may be a concentration of at least one metal selected from Fe, Na, Ca and Mg of the PFT process stream. Other elements, such as chloride, could also be monitored and used for process control.

It is of interest to control element composition chemistry present in free-water and/or emulsified water. Water content in diluted bitumen can be divided soluble-water content and non-soluble water (including free water and emulsified water) content. The soluble-water present in hydrocarbon phases would be intimately associated with the hydrocarbon phase. As soluble-water is miscible with hydrocarbons, it forms a homogeneous phase and the soluble-water would not settle. Soluble-water is generally considered as "pure" water carried in the hydrocarbon phase, and may simply follow the hydrocarbon phase's flow through the unit operation, e.g., upward in the settling vessel. Non-soluble water, including "free" and/or "emulsified" water, is process water (e.g., RCW) that may be carried over if the flux in the settling vessel becomes too high or if process-aids are overdosed. Non-soluble water also includes salts that can corrode equipment. The free- and/or emulsified-water is generally present in the hydrocarbon phase as droplets that will tend to sink in the hydrocarbon phase due to density differences.

EXPERIMENTATION, MODELLING & RESULTS

Diluted bitumen samples were generated via bench scale PFT experimental tests using different types of ores and process water. Dry bitumen product samples were obtained after removing solvent from diluted bitumen. Metal element analysis in bitumen product samples was performed by inductively coupled plasma mass spectroscopy (Agilent 7700 ICP-MS™), which is closely based on ASTM D8110. The composition and mineralogy of three sample ore solids used to prepare the diluted bitumen samples for the bench scales PFT tests were obtained. Water chemistries of five sample process water used to prepare the diluted bitumen samples for the bench scales PFT tests were also obtained. The metal elemental content in the dried bitumen product samples were then obtained.

Experimental results showed that calcium concentration in bitumen product samples increased when caustic dosage increased in primary extraction. The results clearly showed that process water chemistry also affects calcium concentration in bitumen product. Relatively higher calcium and iron concentrations were obtained for certain bitumen product samples, even without caustic addition but when process water, showing that process water composition plays a relevant role in the final composition of the bitumen product. This result could be for example attributed to different clay-ion exchange reactions with process water. Higher calcium concentration in bitumen product can also be attributed to higher calcium naphthanate formation in the primary extraction. Because of their hydrophobic properties, calcium naphthanate will dissolve into diluted bitumen when pentane is added in paraffinic froth treatment.

In addition, overall iron concentration in bitumen product samples reduced with caustic addition in primary extraction. XRD/XRF analyses of certain ores solids were performed and revealed that iron compounds in ore V were pyrite ($FeS_2$), siderite ($FeCO_3$), and other heavy minerals and clays with iron-bearing such as chlorite. Because these iron compounds are more hydrophobic, they likely remained in the diluted bitumen froth, but were removed by asphaltenes rejection.

Various aspects of NIR spectrometry have been studied in the context of PFT operations. Experimentation, chemometric modelling information, and other results are described below. Note that different spectral calibration models are used to detect high concentrations vs. low concentrations of the metal component.

Equipment for the experimentation included a Bruker Matrix™ FT-NIR analyzer with transmission and reflectance probes was used for NIR measurements and analyses. Also, Bruker OPUS Spectroscopy software was used for processing NIR spectra.

In order to evaluate the feasibility and reliability of using online NIR analyzers for operational control and product/stream quality control, the following steps were conducted:

1. QA/QC of Laboratory Data for NIR Modeling—Verification of the data integrity, and use of a relationship between density, and hydrocarbon content (bitumen, solvent and asphaltenes), to identify potential errors in the lab data;
2. Building NIR Models—Building chemometric models for each component (bitumen content, solvent content, asphaltenes content, solids content, water content), and for S/B and density using the OPUS/QUANT™ software in calibrating the NIR spectra via their respective laboratory data;
3. Quantitative Analysis of Unknown Samples—Using developed NIR models to predict S/B, density, and the composition of diluted bitumen.
4. Comparing with RI Measurement—The NIR generated S/B were compared to the RI generated S/B to identify a possible correlation between the outputs of both monitoring instruments.

NIR Calibration Model for Measuring Nickel and Vanadium Concentrations in Bitumen Product QA/QC of Lab Data for NIR Modeling Quality assurance and quality control (QA/QC) was realized to confirm and ensure accuracy of the calibration model.

Figure 4:
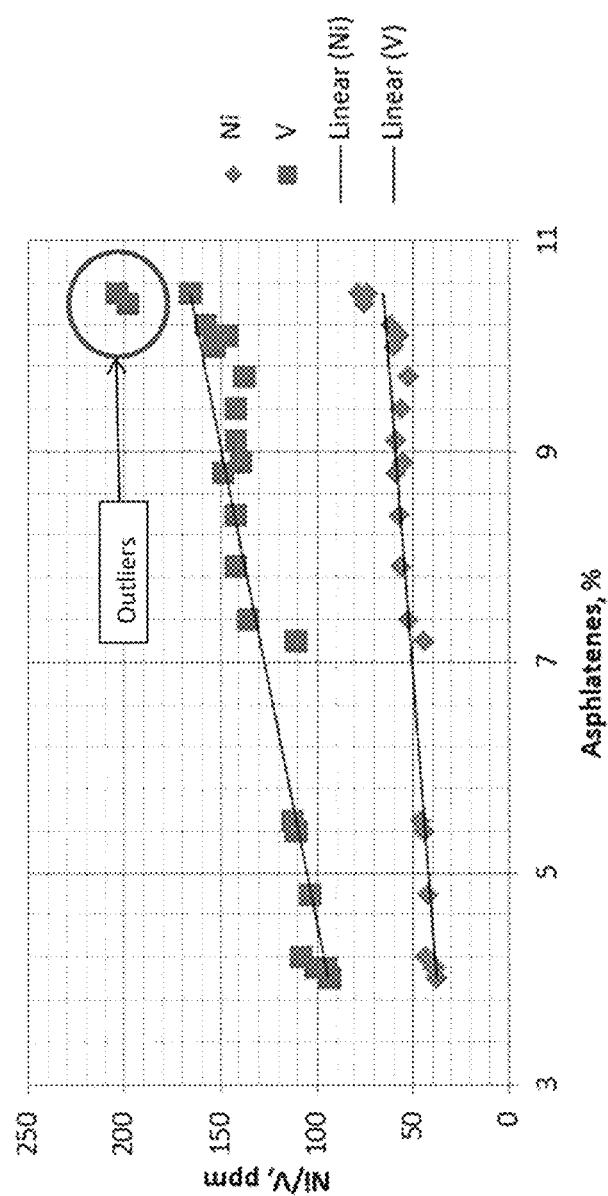
FIGS. 4 and 5 are graphs showing correlations of vanadium and nickel concentrations with asphaltene content in bitumen product.

FIGS. 4 and 5 show that there is a correlation between nickel or vanadium concentrations and asphaltene content of the bitumen product. FIG. 4 illustrates a first step of the method where specific data points are identified as outliers and are discarded for building NIR models and RI correlation. For example, two data points were treated as outliers for vanadium concentration correlation with asphatenes content. FIG. 5 shows that an updated and enhanced correlation was obtained after outliers for nickel and vanadium were removed.

Developing NIR Models

Multivariate calibration (Chemometric methods, i.e. PLS, PCA) were used to build the following models that correlate the acquired NIR spectra to the residual metal concentration of interest, determined via laboratory analysis of samples. Such calibration was performed in the OPUS/QUANT Spectroscopy Software which was provided by Bruker.

Figure 3:
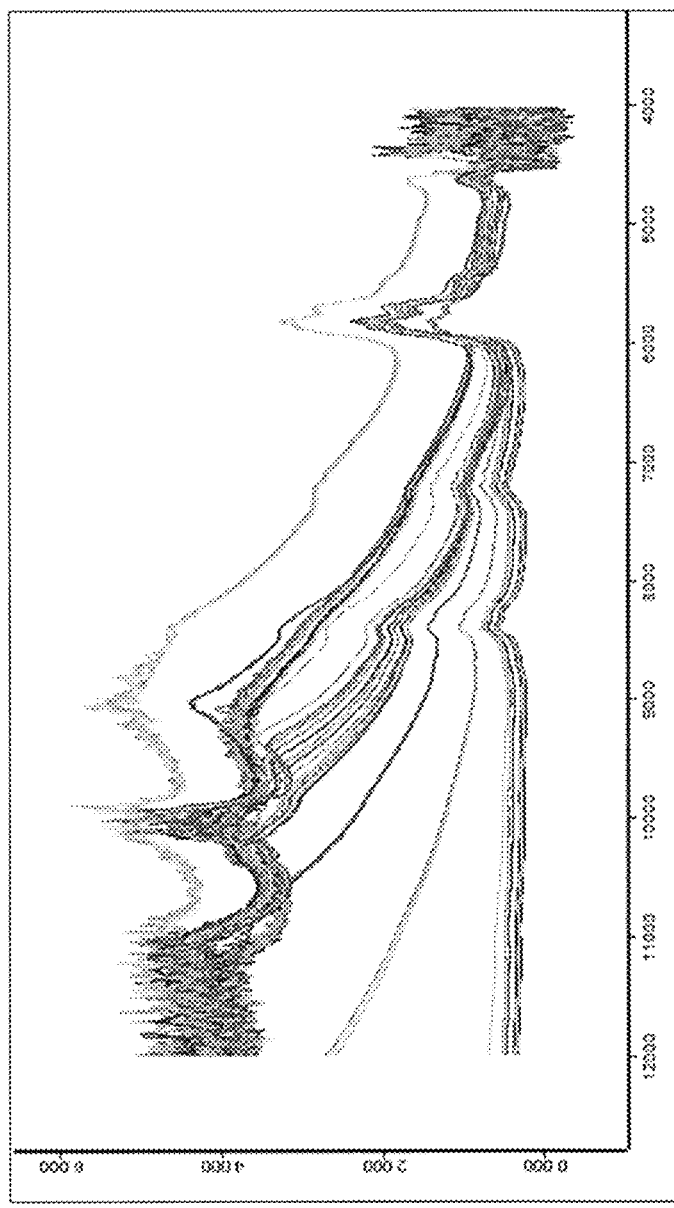
FIG. 3 is a graph of NIR spectra collected from a PFT operation with various process conditions.
Figure 8:
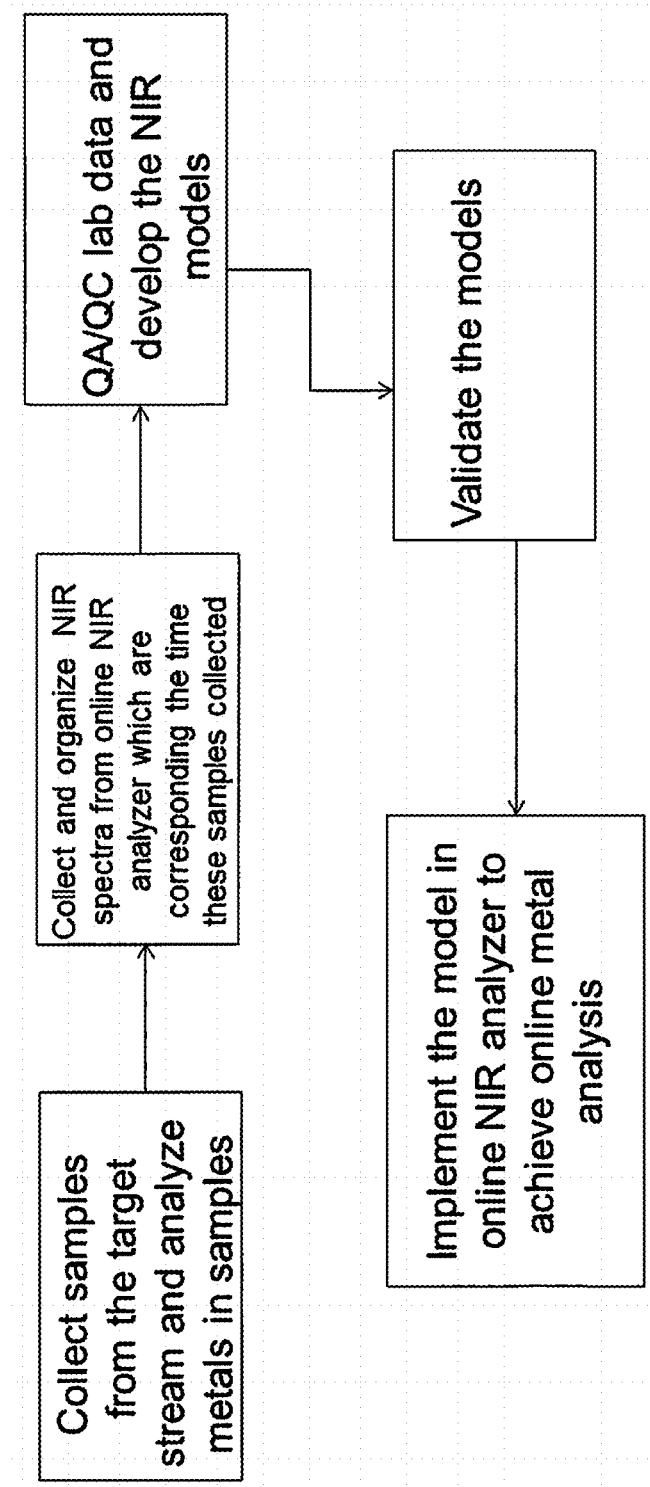
FIG. 8 is a flow chart of an NIR model building work process.
Figure 9:
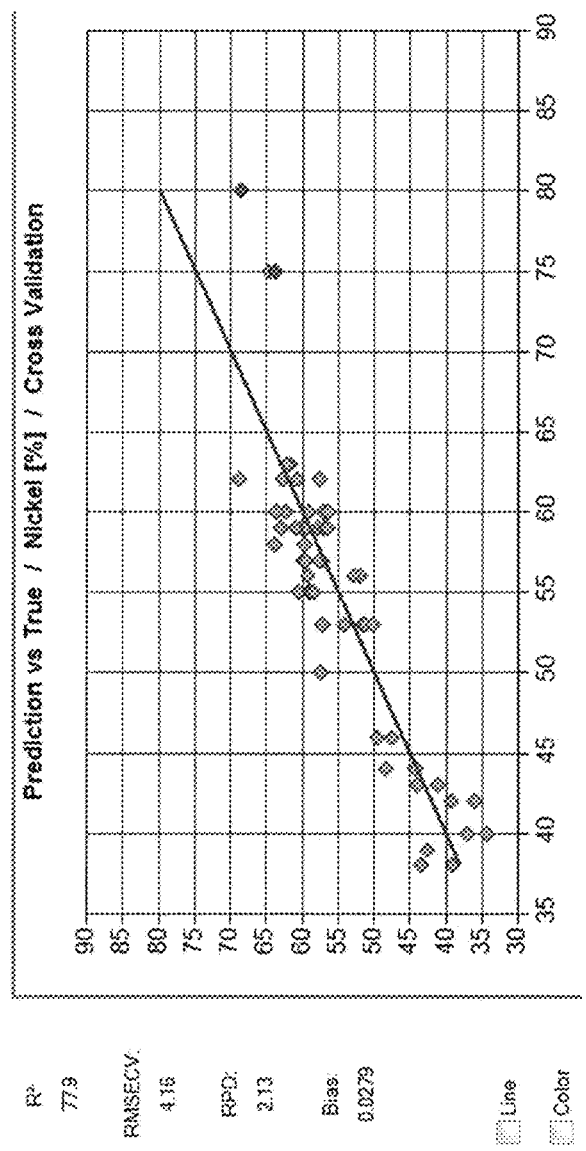
FIG. 9 is an initial calibration model for nickel concentration in a bitumen product.

The modeling process shown in FIG. 8 was completed for all required residual metal concentration measurements. Relevant NIR spectra that were obtained as seen on FIG. 3 are selected and organized according to the time which the lab samples were collected. After compiling the relevant spectra, all of the spectra with available lab data were evaluated using multivariate calibration to identify the outliers which were removed for nickel based on QA/QC analysis (see above and FIGS. 4 and 5). One can see from FIG. 9 that the model did not trend with high correlation. FIG. 9 shows the initial model for the nickel concentration showing a 1/1 line between the predicted and true values.

Figure 10:
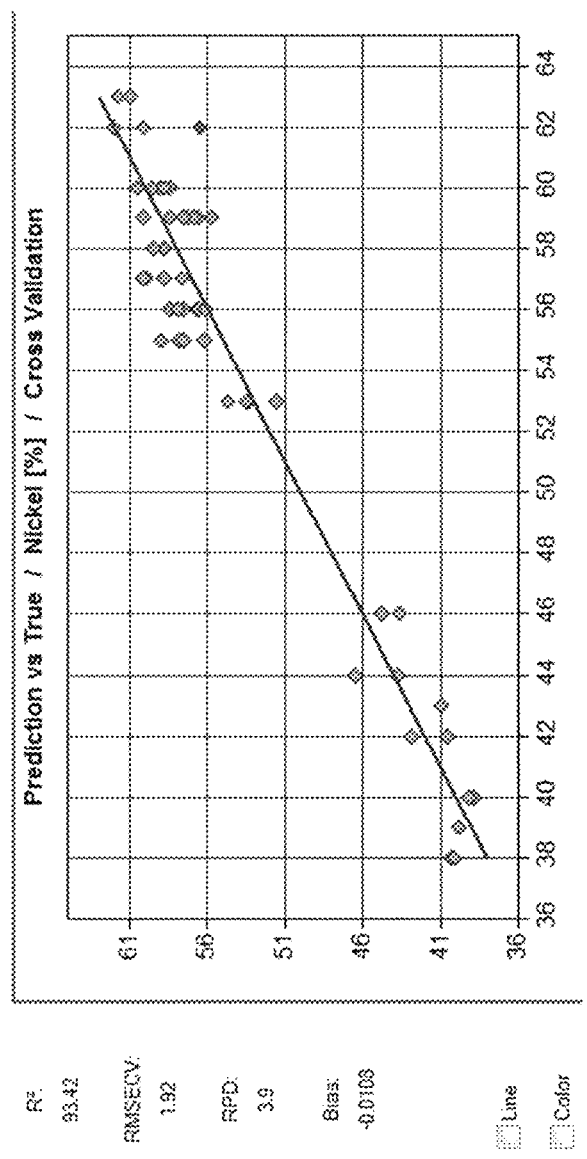
FIG. 10 is a final calibration model for nickel concentration in a bitumen product with outliers removed.

The integrity of the lab data was verified using the asphaltene correlation. Two outlier points were identified as being inconsistent with the data set and were dismissed as lab errors. Upon the removal of these two outliers, the QA/QC improved model was obtained for nickel concentration and is shown in FIG. 10.

The calibration model for nickel concentration was still improved with different data preprocessing methods.

Figure 11:
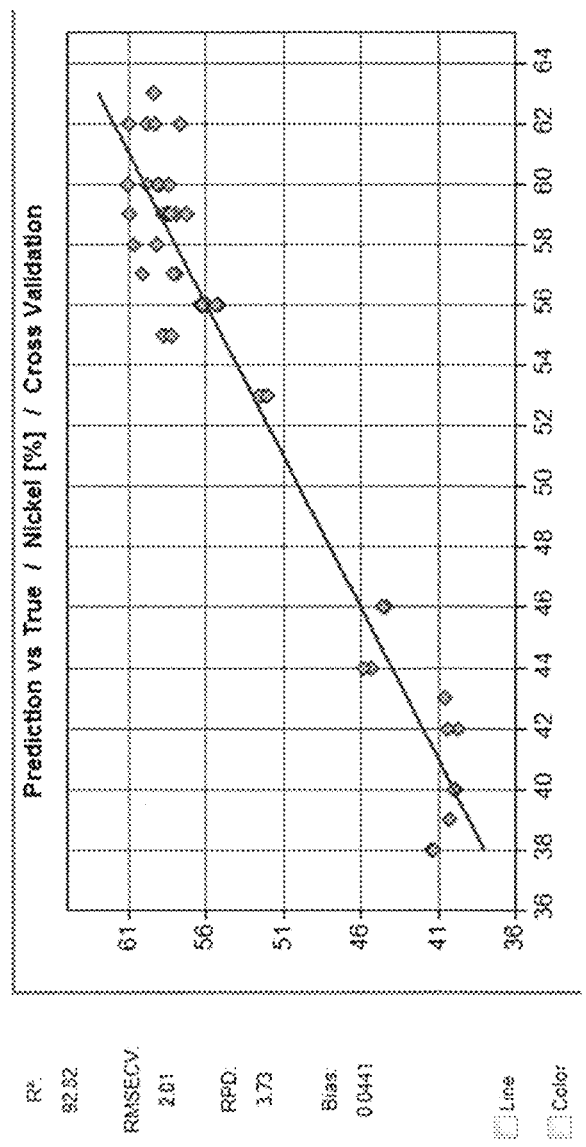
FIG. 11 is a calibration model for nickel concentration with a First Derivative preprocessing method.
Figure 14:
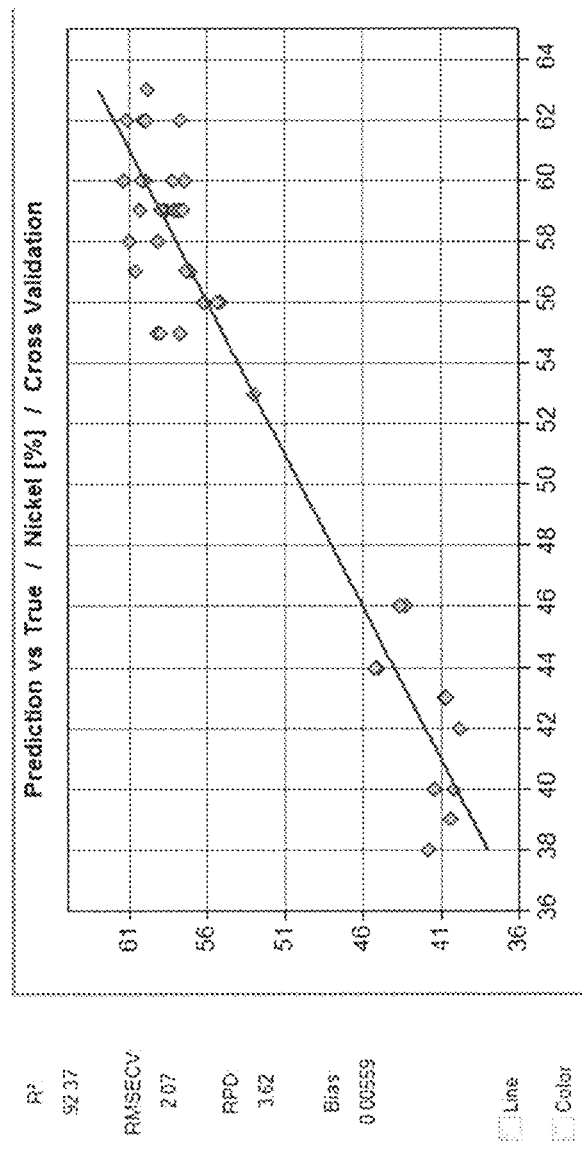
FIG. 14 is a calibration model for nickel concentration with a Second Derivative preprocessing method.

The First Derivative method was used to provide a comparative model shown in FIG. 11 for nickel concentration, and the Second Derivative method was used to provide a comparative model shown in FIG. 14 for nickel concentration. This method involves calculating the first derivative and second derivative of the spectrum respectively, and emphasizes steep edges of a peak which are attributed to the nickel concentration. However spectral noise is also enhanced. FIGS. 11 and 14 show models which are both reasonably accurate.

Figure 12:
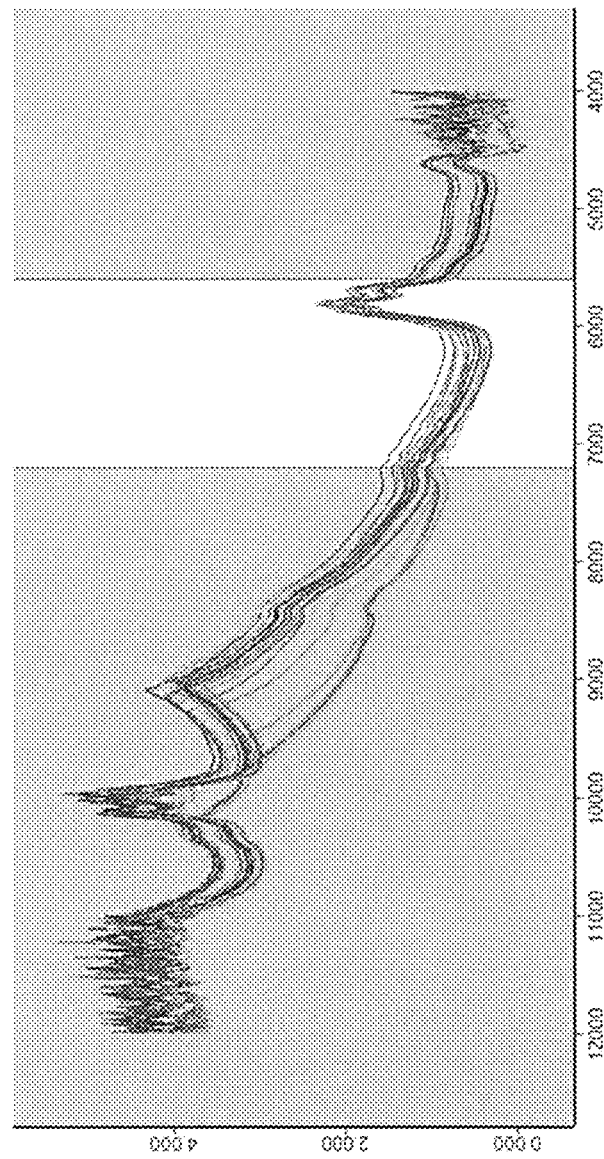
FIG. 12 is a graph showing effective frequency range used for a nickel concentration model with a First Derivative preprocessing method.
Figure 13:
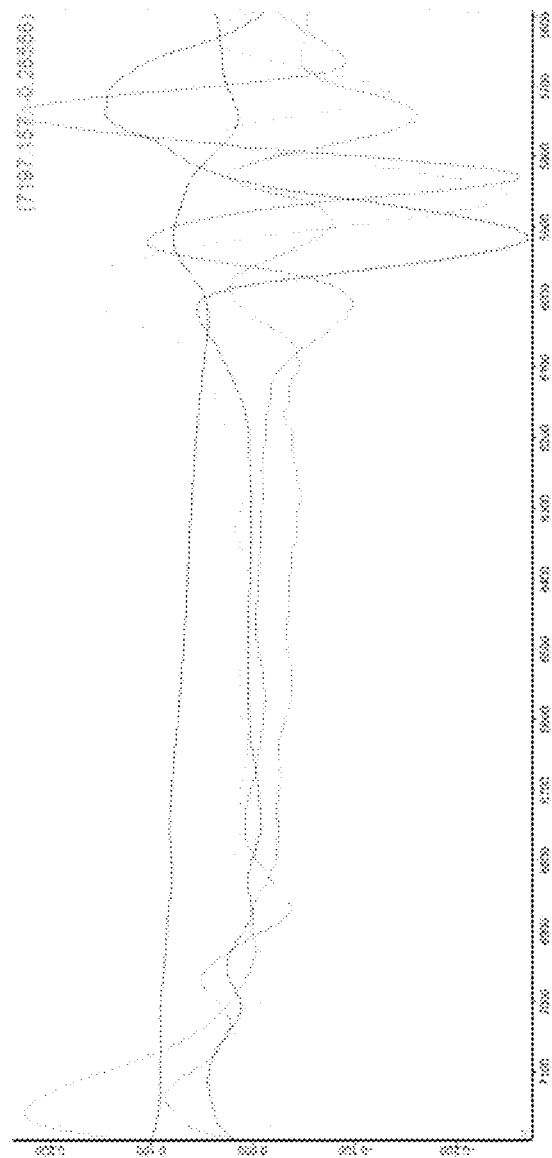
FIG. 13 is a loading plot of the First Derivative spectra used for the nickel concentration model.
Figure 15:
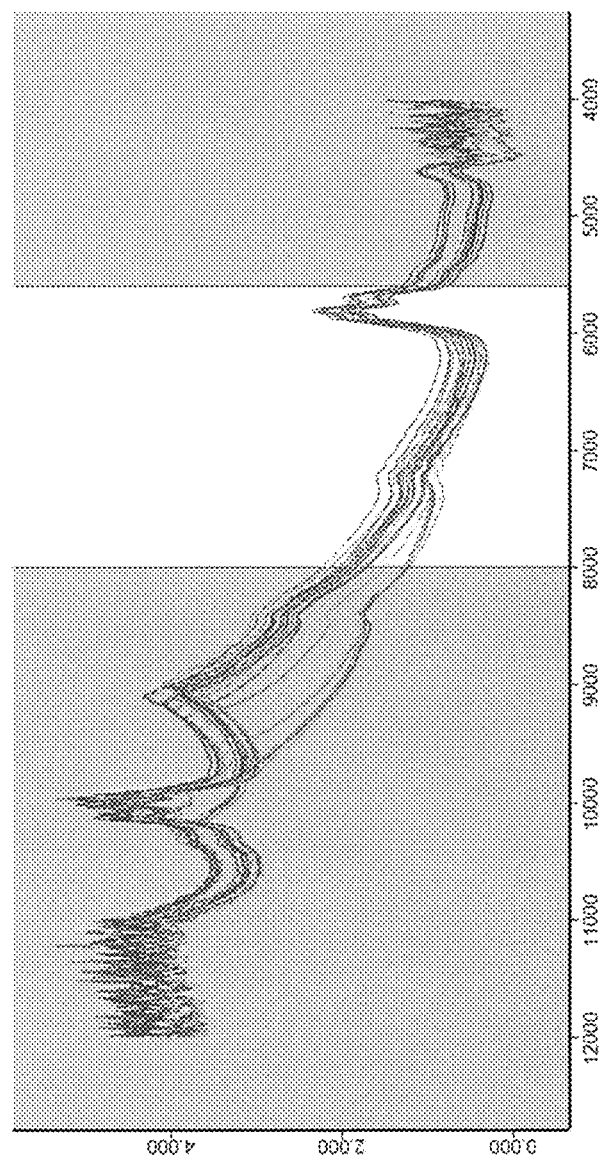
FIG. 15 is a graph showing the effective frequency range used for nickel concentration model with a Second Derivative preprocessing method.
Figure 16:
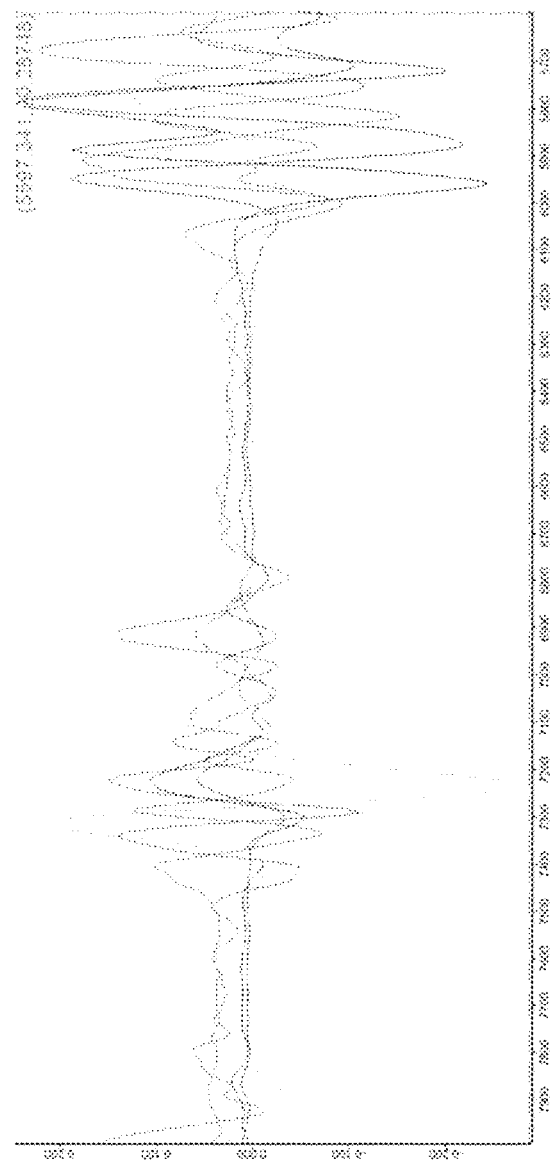
FIG. 16 is a a loading plot of the Second Derivative spectra used for the nickel concentration model.

FIGS. 12, 13 and 15, 16 illustrate the spectrum range used for the modeling. In FIGS. 12 and 15, there are areas of the spectra (grey areas) that show either a lot of spectral noise, or no information. By excluding these areas, and optimizing effective frequencies (white areas between 5500 $cm^{-1}$ and 8000 $cm^{-1}$), there is an increase in accuracy for the chemometric model. Accuracy of the model can be indeed enhanced by eliminating or minimizing variability of the spectra unrelated to the property of interest. As seen on FIGS. 13 and 16, peak overlap can be resolved (and resolution enhanced), and substantially constant and linear baseline drift between samples can be eliminated, by plotting the first and second spectral derivatives versus the frequency range.

For each frequency range, for each data processing method, there is a rank with an associated RMSECV (root mean square error of cross validation). By plotting RMSECV with respect to the rank, the optimal rank for the model can be determined. The root mean square error of cross validation is a measure of the error of the model and is used as criterion to judge the quality of the method. The rank is the number of factors used to represent the model. Too few factors results in an under fit model where many features are not explained. On the other hand, over fitting the model only adds noise and degrades the model. Choosing the optimal rank is tied to the quality of the overall model. Residual Prediction Deviation (RPD) is an important parameter to judge the reliability of the prediction.

The invention claimed is:

1. A process for producing bitumen, comprising:
separating an oil sands slurry in a Primary Separation Vessel (PSV) to produce a bitumen froth and solid-enriched tailings;
feeding the bitumen froth to a Paraffinic Froth Treatment (PFT) operation to produce multiple PFT process streams including a bitumen product stream; and
controlling alkaline agent dosage in the PSV, comprising:
acquiring near infrared (NIR) spectral measurements from an NIR probe located online in at least one of the multiple PFT process streams;
determining a concentration of a residual metal in the at least one PFT process stream based on the acquired NIR spectral measurements;
comparing the determined concentration of residual metal to a concentration specification; and
adjusting the alkaline agent dosage for the PSV in response to a difference between the determined concentration of residual metal and the concentration specification.

2. The process of claim 1, wherein adjusting the alkaline agent dosage comprises at least one of:
changing a nature of the alkaline agent;
increasing the alkaline agent dosage;
decreasing the alkaline agent dosage; and
modifying water dilution of the oil sands slurry.

3. The process of claim 1, wherein the at least one of the multiple PFT process streams is a diluted bitumen overflow from a froth separation unit of the PFT operation.

4. The process of claim 1, wherein the at least one of the multiple PFT process stream is the bitumen product stream from a solvent recovery unit of the PFT operation.

5. The process of claim 1, wherein the residual metal comprises at least one of iron, calcium, sodium and magnesium.

6. The process of claim 5, wherein the concentration specification of calcium is below 10 ppm.

7. The process of claim 5, wherein the concentration specification of sodium is below 100 ppm.

8. The process of claim 1, wherein the NIR probe is a transmittance probe.

9. The process of claim 1, further comprising changing a type of the NIR probe in response to a change in the determined concentration of the residual metal.

10. The process of claim 9, comprising deploying a transmittance type of NIR probe when the PFT operation is in a mature mode and the concentration of the residual metal is expected to be between 1 ppm and 200 ppm.

11. The process of claim 1, wherein the alkaline agent is caustic soda.

12. The process of claim 1, wherein the alkaline agent is caustic soda, sodium silicate, sodium bicarbonate, sodium phosphate or any combination thereof.

13. The process of claim 1, wherein the residual metal is at least one of nickel and vanadium, and the process further comprises adjusting addition of paraffinic solvent into the bitumen froth in the PFT operation in response to a difference between the determined concentration of the at least one of nickel and vanadium and the concentration specification of the at least one of nickel and vanadium.

14. The process of claim 13, wherein the at least one of the multiple PFT streams is a diluted bitumen overflow from a froth separation unit and/or a solvent depleted bitumen stream from a solvent recovery unit that recovers solvent from the diluted bitumen overflow, and adjusting the addition of the paraffinic solvent comprises, in response to an increase in the determined concentration of nickel or vanadium or both, increasing paraffinic solvent addition to obtain an increased solvent-to-bitumen ratio in the bitumen froth.

15. The process of claim 1, wherein the residual metal is at least one of nickel and vanadium, and the process further comprises adjusting asphaltene rejection in a froth separation unit in the PFT operation in response to a difference between the determined concentration of the at least one of nickel and vanadium and the concentration specification of the at least one of nickel and vanadium.

16. The process of claim 15, wherein the at least one of the multiple PFT streams is a diluted bitumen overflow from a froth separation unit and/or a solvent depleted bitumen stream from a solvent recovery unit that recovers solvent from the diluted bitumen overflow, and adjusting the asphaltene rejection comprises, in response to an increase in the determined concentration of nickel or vanadium or both, increasing asphaltene rejection in the froth separation unit.

17. The process of claim 1, wherein the residual metal is calcium and adjusting the alkaline agent dosage for the PSV comprises:
  controlling the alkaline agent dosage into the oil sands slurry in response to the determined calcium concentration when exceeding a predetermined maximum calcium threshold, to provide the at least one of the multiple PFT process streams with a calcium concentration below the predetermined maximum calcium threshold.

18. The process of claim 1, wherein the concentration of each residual metal is at low levels below 1000 ppm.

19. A process for producing bitumen, comprising:
  separating an oil sands slurry in a primary extraction operation to produce a bitumen froth and solid-enriched tailings;
  feeding the bitumen froth to a Paraffinic Froth Treatment (PFT) operation to produce multiple PFT process streams including a bitumen product stream; and
  monitoring quality of the bitumen product stream produced by the PFT operation, comprising:
    acquiring NIR spectral measurements from an NIR probe located online in a diluted bitumen overflow stream and/or the bitumen product stream of the PFT operation; and
    determining a concentration of at least one of vanadium and nickel based on the acquired NIR spectral measurements, wherein the vanadium and nickel are associated with asphaltenes and resins present in the bitumen within the diluted bitumen overflow stream and/or the bitumen product stream, and provide a proxy for the quality of the bitumen product stream.

20. The process of claim 19, wherein the concentration of vanadium and nickel are at low levels below 1000 ppm.

21. A process for producing bitumen comprising:
  separating an oil sands slurry in a Primary Separation Vessel (PSV) to produce a bitumen froth and solid-enriched tailings;
  feeding the bitumen froth to a bitumen froth treatment operation to recover a diluted bitumen overflow in a froth separation unit and further produce bitumen in a solvent separation unit that recovers solvent from the diluted bitumen overflow; and
  controlling the bitumen froth treatment operation, comprising:
    acquiring NIR spectral measurements from an NIR probe located online in at least one of the diluted bitumen overflow and the bitumen;
    determining a concentration of at least one of vanadium and nickel based on the acquired NIR spectral measurements;
    comparing the determined concentration to a concentration specification; and
    controlling a quality of the bitumen in response to a difference between the determined concentration and the concentration specification.

22. The process of claim 21, wherein the concentration specification of nickel is between 50 and 60 ppm.

23. The process of claim 21, wherein the concentration specification of vanadium is between 130 and 160 ppm.

24. The process of claim 21, wherein controlling the quality of the bitumen comprises increasing asphaltene rejection in the froth separation unit, if the determined concentration is above the concentration specification.

25. The process of claim 21, wherein controlling the quality of the bitumen comprises increasing solvent addition to provide a higher solvent-to-bitumen ratio in the bitumen froth that is supplied into the froth separation unit to increase asphaltene precipitation, if the determined concentration is above the concentration specification.

26. The process of claim 21, wherein the bitumen froth treatment operation is a paraffinic froth treatment operation and controlling the quality of the bitumen comprises regulating at least one operating parameter of the paraffinic froth treatment operation.

27. The process of claim 26, wherein the at least one operating parameter of the paraffinic froth treatment operation that is regulated in response to the difference between the determined concentration and the concentration specification comprises a temperature of the froth separation unit, a type of the paraffinic solvent added to the bitumen froth, a pretreatment of the bitumen froth prior to the froth separation unit, a bitumen content of the bitumen froth prior to the froth separation unit, a settling parameter of the froth separation unit, or a combination thereof.

28. The process of claim 21, wherein the concentration of vanadium and nickel are at low levels below 1000 ppm.

\* \* \* \* \*